United States Patent

Yanagisawa et al.

[11] Patent Number: 4,734,410
[45] Date of Patent: Mar. 29, 1988

[54] LACTAM DERIVATIVES AND THEIR USE AS HYPOTENSIVE AGENTS

[75] Inventors: Hiroaki Yanagisawa; Sadao Ishihara; Akiko Ando; Takuro Kanazaki; Hiroyuki Koike; Yasuteru Iijima, all of Hiromachi, Japan

[73] Assignee: Sankyo Company Limited, Tokyo, Japan

[21] Appl. No.: 917,041

[22] Filed: Oct. 9, 1986

[30] Foreign Application Priority Data

Oct. 11, 1985 [JP] Japan ................. 60-226044

[51] Int. Cl.[4] .............. C07D 225/02; C07D 223/10; A61K 31/55; A61K 31/395
[52] U.S. Cl. ................. 514/212; 514/183; 514/321; 540/527; 540/524; 540/463; 546/223
[58] Field of Search .............. 540/463, 524, 527; 546/223; 514/183, 212, 327

[56] References Cited

U.S. PATENT DOCUMENTS

| | | | |
|---|---|---|---|
| 4,587,050 | 5/1986 | Harris et al. | 546/463 |
| 4,629,787 | 12/1986 | Harris et al. | 540/527 |
| 4,680,392 | 7/1987 | Harris et al. | 540/527 |
| 4,699,905 | 11/1987 | Yanagisawa et al. | 514/211 |

FOREIGN PATENT DOCUMENTS 0046291 2/1982 European Pat. Off. ........... 540/524
0161801 11/1985 European Pat. Off. ......... 428/312.6

OTHER PUBLICATIONS

Eugene D. Thorsett et al., Peptides Structure and Function, American Peptide Symposium (8th: 1983: University of Arizona), pp. 556-558.

*Primary Examiner*—Robert T. Bond
*Attorney, Agent, or Firm*—Frishauf, Holtz, Goodman & Woodward

[57] ABSTRACT

Compounds of formula (I):

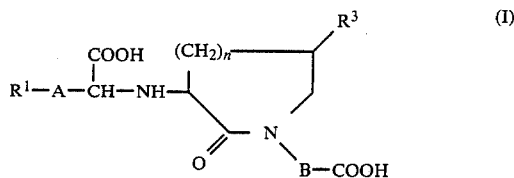

(wherein $R^1$ and $R^3$ are organic groups, A is a direct bond, $-CH_2-$, $-CH_2CH_2-$, $-CO-CH_2$, $-O-CH_2-$ or $-S-CH_2-$, B is lower alkylene and n is 1-3) are valuable hypotensive agents which may be prepared by a condensation reaction of the corresponding compound having an amino group at the 3-position.

27 Claims, No Drawings

LACTAM DERIVATIVES AND THEIR USE AS HYPOTENSIVE AGENTS

BACKGROUND TO THE INVENTION

The present invention relates to a series of lactam derivatives which have the valuable ability to lower blood pressure and which are hence of potential use in the treatment of humans and other animals suffering from elevated blood pressure.

There is considerable evidence that reduction of elevated blood pressure reduces the risks of morbidity and mortality. Elevated blood pressure (hypertension) can be caused by a variety of factors and a large number of drugs is available for the treatment of hypertension, the drug of choice being dictated in large measure by the cause of the hypertension, as well as the degree of hypertension and the acceptance of the treatment by the patient. One of the known causes of hypertension is the presence in blood plasma of the polypeptide known as angiotensin II, and a reduction in the blood plasma levels of angiotensin II has been shown to reduce hypertension. The first step in the production of angiotensin II in the mammalian body is the conversion of a blood protein, by the enzyme renin, to a polypeptide known as "angiotensin I". This angiotensin I is then converted by angiotensin converting enzyme (hereinafter referred to, as is conventional, as "ACE") to angiotensin II. The enzyme ACE has another metabolic function, namely it participates in the metabolism of bradykinin, a natural vasodilator, converting it to an inactive metabolite.

Hence, the enzyme, ACE is capable of raising blood pressure by two routes: one is the production of angiotensin II, which itself raises blood pressure; the second is the inactivation of bradykinin which, through its vasodilatory activity, tends to reduce blood pressure. There has, therefore, been considerable interest in recent years in the development of compounds having the ability to inhibit the activity of ACE.

We have now discovered a series of lactam derivatives which have this ability. The compounds of the invention have either 6, 7 or 8 ring atoms in the lactam system and can thus be regarded as 1,3,5-trisubstituted piperidin-2-one derivatives, 1,3,6-trisubstituted perhydroazepin-2-one derivatives or 1,3,7-trisubstituted perhydroazocin-2-one derivatives, according to whether they have 6, 7 or 8 ring atoms.

The closest prior art is believed to be European Patent Publication No. 46,291, which discloses a series of perhydroazepin-2-one (or caprolactam) derivatives having substituents at the 1- and 3-positions and optionally also having a substituent at the 7-position. The compounds of European Patent Publication No. 46,291, however, unlike the compounds of the present invention, are unsubstituted at the 6-position. Surprisingly, we have found that the compounds of the present invention have several advantages over the prior art compounds of European Patent Publication No. 46,291, including a higher ACE inhibitory activity and a longer duration of this activity in vivo.

BRIEF SUMMARY OF INVENTION

The compounds of the invention are those compounds of formula (I):

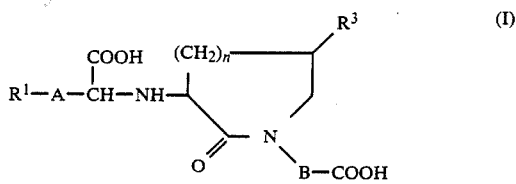

in which:

$R^1$ represents a $C_1$-$C_{10}$ alkyl group, a $C_3$-$C_8$ cycloalkyl group, a $C_6$-$C_{14}$ aryl group or a heterocyclic group having from 4 to 14 ring atoms, of which from 1 to 5 are hetero-atoms selected from the group consisting of nitrogen, oxygen and sulfur atoms, or said alkyl group having at least one substituent selected from the group consisting of substituents (a) or said cycloalkyl, aryl or heterocyclic group having at least one substituent selected from the group consisting of substituents (a) and substituents (b);

$R^3$ represents a $C_1$-$C_{10}$ alkyl group, a $C_3$-$C_8$ cycloalkyl group, an aralkyl group wherein the alkyl part is $C_1$-$C_6$ alkyl and the aryl part is $C_6$-$C_{10}$ carbocyclic aryl, a $C_6$-$C_{14}$ aryl group, a $C_1$-$C_6$ alkyl group having a heterocyclic substituent or a heterocyclic group, where said heterocyclic group or said heterocyclic substituent has from 4 to 14 ring atoms, of which from 1 to 5 are hetero-atoms selected from the group consisting of nitrogen, oxygen and sulfur hetero-atoms, or said alkyl group having at least one substituent selected from the group consisting of substituents (a) or said cycloalkyl, aryl or heterocyclic group having at least one substituent selected from the group consisting of substituents (a) and (b);

A represents a single bond, a methylene group, an ethylene group or a group of formula —CO—CH$_2$—, —O—CH$_2$— or —S—CH$_2$—;

B represents an alkylene group having from 1 to 4 carbon atoms; and n is an integer from 1 to 3;

substituents (a):

hydroxy groups, $C_1$-$C_6$ alkoxy groups, $C_6$-$C_{10}$ carbocyclic aryl groups having from 0 to 3 substituents selected from the group consisting of substituents (a) and substituents (b), aralkyloxy groups where the alkyl part is $C_1$-$C_6$ alkyl and the aryl part is $C_6$-$C_{10}$ carbocyclic aryl which has from 0 to 3 substituents selected from the group consisting of substituents (a) and (b), $C_6$-$C_{10}$ aryloxy groups, halogen atoms, nitro groups, cyano groups, carboxy groups, alkoxycarbonyl groups having a total of from 2 to 7 carbon atoms, amino groups, $C_1$-$C_6$ alkylamino groups, dialkylamino groups wherein each alkyl part is $C_1$-$C_6$ alkyl, aliphatic or carbocyclic aromatic carboxylic acylamino groups, carbamoyl groups, alkylcarbamoyl groups where the alkyl part is $C_1$-$C_6$ alkyl, dialkylcarbamoyl groups where each alkyl part is $C_1$-$C_6$ alkyl, mercapto groups, $C_1$-$C_6$ alkylthio groups, $C_6$-$C_{10}$ carbocyclic arylthio groups, $C_1$-$C_6$ alkylsulfonyl groups and $C_6$-$C_{10}$ carbocyclic arylsulfonyl groups wherein the aryl part has from 0 to 3 $C_1$-$C_6$ alkyl substituents;

substituents (b):

$C_1$-$C_6$ alkyl groups and aralkyl groups wherein the alkyl part is $C_1$-$C_6$ alkyl and the aryl part is $C_6$-$C_{10}$ carbocyclic aryl which has from 0 to 3 substituents selected from the group consisting of substituents (a) and substituents (b);

and pharmaceutically acceptable salts and esters thereof.

The invention also provides a pharmaceutical composition for the treatment of angiotensin-induced hypertension, which composition comprises a hypotensive agent in admixture with a pharmaceutically acceptable carrier or diluent, wherein said hypotensive agent is selected from the group consisting of compounds of formula (I) and pharmaceutically acceptable salts and esters thereof.

The invention still further provides a method of treating angiotensin-induced hypertension in a mammal, which may be human or non-human, by administering to said mammal an effective amount of a hypotensive agent, wherein said hypotensive agent is selected from the group consisting of compounds of formula (I) and pharmaceutically acceptable salts and esters thereof.

The invention also provides processes for preparing the compounds of the invention, which are described in more detail hereafter.

DETAILED DESCRIPTION OF INVENTION

In the compounds of the invention, $R^1$ may represent an alkyl group, a cycloalkyl group, an aryl group or a heterocyclic group.

Where $R^1$ represents an alkyl group, this may be a straight or branched chain alkyl group which has from 1 to 10, more preferably from 1 to 8, carbon atoms. Examples of such groups include the methyl, ethyl, propyl, isopropyl, butyl, isobutyl, t-butyl, pentyl, neopentyl, hexyl and octyl groups.

Where $R^1$ represents a cycloalkyl group, this has from 3 to 8, more preferably from 5 to 7, ring carbon atoms and examples of such groups include the cyclopentyl, cyclohexyl and cycloheptyl groups.

Where $R^1$ represents an aryl group, this is preferably a carbocyclic aryl group which has from 6 to 14, more preferably from 6 to 10, ring carbon atoms and may comprise a single or multiple (fused) ring system. Preferred examples of such aryl groups include the phenyl, 1-naphthyl and 2-naphthyl groups.

Where $R^1$ represents a heterocyclic group, this may be a saturated or unsaturated heterocyclic group and may be monocyclic or polycyclic (preferably bicyclic); it has from 4 to 14, preferably from 5 to 10, ring atoms, of which from 1 to 5, more preferably from 1 to 3, are hetero-atoms selected from the group consisting of nitrogen, oxygen and sulfur hetero-atoms. Where the heterocyclic ring is unsaturated, it may be aromatic or non-aromatic. Examples of such heterocyclic groups include the tetrahydrofuranyl, tetrahydrothienyl, tetrahydropyranyl, morpholinyl, furyl, thienyl, imidazolyl, thiazolyl, oxazolyl, isoxazolyl, thiadiazolyl (e.g. 1,3,4-thiadiazolyl), oxadiazolyl (e.g. 1,3,4-oxadiazolyl), pyridyl, quinolyl, isoquinolyl and indolyl groups.

These groups represented by $R^1$ may be unsubstituted or may have at least one substituent selected from the following groups:

Except where the group represented by $R^1$ is itself an alkyl group, $C_1-C_6$, preferably $C_1-C_4$, alkyl groups, for example the methyl, ethyl, propyl, isopropyl, butyl, isobutyl and t-butyl groups;

$C_6-C_{10}$ carbocyclic aryl groups, which may be monocyclic or fused polycyclic (preferably bicyclic) groups and which may themselves be substituted as here defined, particularly the phenyl, 1-naphthyl or 2-naphthyl groups;

except where the group represented by $R^1$ is an alkyl group, aralkyl groups in which the alkyl part is $C_1-C_6$ alkyl and the aryl part is $C_6-C_{10}$ carbocyclic aryl, for example the benzyl, phenethyl, 1-napthylmethyl, 2-naphthylmethyl and 3-phenylpropyl groups;

the hydroxy group;

$C_1-C_6$, preferably $C_1-C_4$, alkoxy groups, for example the methoxy, ethoxy, propoxy, isopropoxy, butoxy or isobutoxy groups;

aralkyloxy groups, in which the aryl part is $C_6-C_{10}$ carbocyclic aryl, more preferably phenyl, and the alkyl part is $C_1-C_6$ alkyl, more preferably $C_1-C_2$ alkyl and most preferably methyl, for example the benzyloxy group;

aryloxy groups, in which the aryl part is $C_6-C_{10}$ carbocyclic aryl, more preferably phenyl, for example the phenoxy group;

halogen atoms, for example the fluorine, chlorine and bromine atoms;

the nitro, cyano and carboxy groups;

alkoxycarbonyl groups, in which the alkoxy part is $C_1-C_6$, more preferably $C_1-C_3$, alkoxy, for example the methoxycarbonyl and ethoxycarbonyl groups;

the amino group;

alkylamino groups in which the alkyl part is $C_1-C_6$, more preferably $C_1-C_4$, alkyl, for example the methylamino and ethylamino groups;

dialkylamino groups, in which each alkyl part is $C_1-C_6$, preferably $C_1-C_4$, more preferably $C_1-C_3$, alkyl, for example the dimethylamino or diethylamino groups;

acylamino groups, which can be aliphatic carboxylic acylamino groups, preferably having from 1 to 7, more preferably from 1 to 4, carbon atoms or carbocyclic aromatic carboxylic acylamino groups in which the aromatic part is $C_6-C_{10}$ carbocyclic aryl and is more preferably a phenyl group, for example the acetamido and benzamido groups;

the carbamoyl group;

the alkylcarbamoyl and dialkylcarbamoyl groups, in which the or each alkyl part is $C_1-C_6$, more preferably $C_1-C_4$ and most preferably $C_1-C_3$, alkyl, for example the N-methylcarbamoyl, N-ethylcarbamoyl, dimethylcarbamoyl or diethylcarbamoyl groups;

the mercapto group;

$C_1-C_6$, more preferably $C_1-C_4$, alkylthio groups, for example the methylthio or ethylthio groups;

arylthio groups in which the aryl part is $C_6-C_{10}$ carbocyclic aryl, more preferably phenyl, for example the phenylthio group;

$C_1-C_6$, more preferably $C_1-C_4$, alkylsulfonyl groups, for example the methanesulfonyl or ethanesulfonyl groups;

arylsulfonyl groups in which the aryl part is $C_6-C_{10}$ carbocyclic aryl, more preferably phenyl, for example the benzenesulfonyl group.

Where the group represented by $R^1$ is substituted, the maximum number of substituents will, of course, depend upon the size of the group to be substituted and the steric effects exerted by the substituents; if the group represented by $R^1$ is small, for example a lower alkyl group, and the substituent bulky, then steric hindrance may limit the number of potential substituents; at the other extreme, if the substituent is small, the number of susbstituents may only be limited by the number of available valencies of the atoms in the group represented by $R^1$. For example, where the substituent is a fluorine or chlorine atom, $R^1$ could represent a perfluoroalkyl or perchloroalkyl group. However, in general, from 1 to 3 substituents are preferred, although it should be appreciated that more may be appropriate in specific cases, as is well recognized by those skilled in the chemical arts.

$R^3$ can represent an alkyl, cycloalkyl, aralkyl, aryl, heterocyclic-substituted alkyl or heterocyclic group.

Where $R^3$ represents an alkyl group, this is a $C_1$-$C_{10}$ alkyl group, which may be a straight or branched chain group, more preferably having from 1 to 8 carbon atoms. Examples of such groups include the methyl, ethyl, propyl, isopropyl, butyl, isobutyl, sec-butyl, t-butyl, pentyl, isopentyl, neopentyl, hexyl, heptyl and octyl groups.

Where $R^3$ represents a cycloalkyl group, this has from 3 to 8, more preferably from 5 to 7, ring carbon atoms and preferred such groups include the cyclopentyl, cyclohexyl and cycloheptyl groups.

Where $R^3$ represents an aralkyl group, the alkyl part is a $C_1$-$C_6$, more preferably $C_1$-$C_4$ and most preferably $C_1$-$C_3$, alkyl group (examples being those $C_1$-$C_6$ alkyl groups included amongst the examples of alkyl groups which may be represented by $R^1$) and the aryl part is a $C_6$-$C_{10}$ carbocyclic aryl group (examples of which are those groups given as examples of aryl groups which may be represented by $R^1$), preferably a phenyl group. Preferred aralkyl groups are the benzyl, phenethyl and 3-phenylpropyl groups.

Where $R^3$ represents a carbocyclic aryl group, this has from 6 to 14, preferably from 6 to 10, ring carbon atoms and may be a monocyclic or fused polycyclic (normally bicyclic) group. Preferred examples include the phenyl, 1-naphthyl and 2-naphthyl groups.

Where $R^3$ represents a heterocyclic group or an alkyl group having a heterocyclic substituent, the heterocyclic group has from 4 to 14, preferably from 5 to 10, more preferably from 5 to 8, ring atoms, of which from 1 to 5, more preferably from 1 to 3, are hetero-atoms selected from the group consisting of nitrogen, sulfur and oxygen atoms. The heterocyclic group may be saturated, unsaturated or partially saturated, preferably saturated or unsaturated, and may be monocyclic or fused polycyclic (preferably bicyclic). Examples of such groups include the tetrahydrofuranyl, tetrahydrothienyl, tetrahydropyranyl, morpholinyl, furyl, thienyl, imidazolyl, thiazolyl, oxazolyl, isoxazolyl, oxadiazolyl (e.g. 1,3,4-oxadiazolyl), thiadiazolyl (e.g. 1,3,4-thiadiazolyl), pyridyl, quinolyl, isoquinolyl and indolyl groups. Where $R^3$ represents an alkyl group having such a heterocyclic substituent, the alkyl group itself is a $C_1$-$C_6$, preferably $C_1$-$C_4$ and more preferably $C_1$-$C_3$, alkyl group (which may be a straight or branched chain group) and examples of such groups are the $C_1$-$C_6$ groups amongst those given as examples of alkyl groups which may be represented by $R^1$.

The groups defined above for $R^3$ may be unsubstituted or may have at least one substituent selected from those substituents defined in (a) and/or (b) above and exemplified as substituents on the groups represented by $R^1$. As with $R^1$, where any group represented by $R^3$ is substituted, the number of substituents is only limited by steric considerations, which, of course, vary depending upon the nature of the substituent and the substituted groups and so cannot be defined in general terms. Normally, however, it is convenient, where such groups are substituted, to have from 1 to 3 substituents, but it should be appreciated that this does not, in any sense, represent a practical limit.

The symbol A can represent a direct single bond between the group represented by $R^1$ and the carbon atom of the group CH—NH at the 3-position of the lactam ring; alternatively, it can represent a methylene group, an ethylene group, a carbonylmethyl (—CO—CH$_2$—) group, an oxymethyl (—OCH$_2$—) group or a thiomethyl (—SCH$_2$—) group. We prefer that A should represent an ethylene group and more particularly prefer that the group represented by $R^1$—A— should be:

a straight or branched chain alkyl group having from 4 to 9 carbon atoms, for example a butyl, isobutyl, pentyl, isopentyl, neopentyl, hexyl, octyl, isooctyl or nonyl group;

a 2-cycloalkylethyl group, in which the cycloalkyl part has 5 or 6 ring carbon atoms, for example a 2-cyclopentylethyl or 2-cyclohexylethyl group;

an aralkyl group having a total of from 7 to 12 carbon atoms, for example a benzyl, phenethyl, 1-naphthylmethyl, 2-naphthylmethyl, 2-(1-naphthyl)ethyl or 2-(2-naphthyl)ethyl group;

a phenoxymethyl or phenylthiomethyl group; or a heterocyclic-substituted ethyl group, for example a 2-(2-thienyl)ethyl, 2-(2-imidazoyl)ethyl or 2-(2-thiazolyl)ethyl group.

n may be 1, 2 or 3, but is most preferably 2 or 3.

B may represent a $C_1$-$C_4$ alkylene group. The two "free" valencies of the alkylene group may be attached to the same carbon atom (in which case the group is sometimes referred to as an "alkylidene" group) or they may be attached to different carbon atoms. Examples of such alkylene groups which may be represented by B are the methylene, ethylene, trimethylene, tetramethylene, ethylidene, propylidene and butylidene groups, preferably the methylene, ethylene and ethylidene groups. B most preferably represents a methylene group.

The compounds of formula (I) have two free carboxy groups and can thus form mono- or di- esters with appropriate ester-forming groups. There is no practical limitation upon the nature of the ester-forming groups employed in this invention, beyond the practical consideration that, if the resulting compounds are in themselves to be used for the treatment of human beings or other animals, the resulting esters must be "pharmaceutically acceptable"; this, as is well known to the skilled man, means that the ester-forming groups must not, or must not to an unacceptable extent, reduce the activity in vivo or increase the toxicity of the compounds. Where the resulting compounds are not in themselves to be used as medicines but, instead, are to be used as intermediates in the preparation of other compounds, even this practical restriction does not apply and any ester appropriate to the intended preparative route may be formed.

The resulting compounds of the invention may be represented by the formula (Ia):

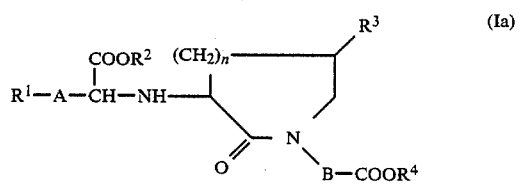

(wherein $R^1$, $R^3$, A, B and n are as defined above and $R^2$ and $R^4$, which are the same or different, each represents a hydrogen atom or a carboxy-protecting, preferably ester-forming, group).

The carboxy-protecting group represented by $R^2$ and $R^4$ may be any such group known in organic synthesis, although it is preferably an ester residue which is capable of easy hydrolysis in vivo (normally in the mammalian body, e.g. blood stream or enteric system) to the free acid, particularly with regard to $R^2$.

Preferably, $R^2$ and $R^4$ are the same or different and each represents a $C_1$–$C_{10}$ alkyl group, an aralkyl group in which the aryl part is a $C_6$–$C_{10}$ carbocyclic aryl group which is unsubstituted or substituted as defined in (c) below and the alkyl part is $C_1$–$C_6$ alkyl, a $C_6$–$C_{14}$ carbocyclic aryl group, a phthalidyl group or a substituted silyl group, e.g. a trialkylsilyl group where each alkyl part is $C_1$–$C_6$ alkyl, said groups represented by $R^2$ and $R^4$ being unsubstituted or having at least one substituent selected from the group consisting of:

(c) $C_1$–$C_6$ alkyl groups (except where the parent group is an alkyl group), halogen atoms, hydroxy groups, $C_1$–$C_6$ alkoxy groups, ($C_1$–$C_6$ alkoxy)-($C_1$–$C_3$ alkoxy) groups, aliphatic and carbocyclic aromatic carboxylic acyloxy groups, oxo groups, carboxy groups, alkoxycarbonyl groups where the alkoxy part is $C_1$–$C_6$ alkoxy, alkoxycarbonyloxy groups where the alkoxy part is $C_1$–$C_6$ alkoxy, aliphatic and carbocyclic aromatic carboxylic acylamino groups, nitro groups, cyano groups, amino groups, $C_1$–$C_6$ alkylamino groups, dialkylamino groups where each alkyl part is $C_1$–$C_6$ alkyl, $C_6$–$C_{10}$ carbocyclic arylamino groups, mercapto groups, $C_1$–$C_6$ alkylthio groups, $C_6$–$C_{10}$ carbocyclic arylthio groups, $C_1$–$C_6$ alkylsulfonyl groups, $C_6$–$C_{10}$ carbocyclic arylsulfonyl groups and heterocyclic groups having from 5 to 14 ring atoms, of which from 1 to 5 are hetero-atoms selected from the group consisting of nitrogen, sulfur and oxygen atoms, said heterocyclic groups being unsubstituted or having at least one substituent selected from the group consisting of the substituents defined in (a) and (b) above.

Examples of the above substituents have either been given previously in relation to substituents on $R^1$ or are combinations of substituents exemplified previously.

If desired, the alkyl part of the aralkyl group may be attached to two carbon atoms of the aryl group via two of its carbon atoms to form a partially unsaturated, non-aromatic ring (the unsaturation arising from the carbon atoms of the aryl group) through which this aralkyl group is attached to the remainder of the molecule of the compound of formula (I). Alternatively, the aryl group and the alkyl group may be attached to each other through one carbon atom of each group.

Examples of such groups which may be represented by $R^2$ and $R^4$ include:

$C_1$–$C_6$ alkyl groups, such as the methyl, ethyl, propyl, isopropyl, butyl, isobutyl, t-butyl, pentyl and hexyl groups;

aralkyl and diarylalkyl groups, such as the benzyl, benzhydryl (diphenylmethyl), 1-indanyl, 2-indanyl, 1-(1,2,3,4-tetrahydronaphthyl) and 2-(1,2,3,4-tetrahydronaphthyl) groups;

the phthalidyl group;

$C_6$–$C_{10}$ carbocyclic aryl groups, particularly the phenyl group;

trialkylsilyl groups, particularly the trimethylsilyl and t-butyldimethylsilyl groups; and such groups listed above having one or more substituents selected from the group consisting of alkyl, halogen, hydroxy, alkoxy, alkoxyalkoxy, acyloxy, oxo, carboxy, alkoxycarbonyl, alkoxycarbonyloxy, acylamino, nitro, cyano, amino, alkylamino, dialkylamino, arylamino, alkylthio, arylthio, alkylsulfonyl, arylsulfonyl and 2-oxo-1,3-dioxolen-4-yl (which may itself be substituted) substituents.

Where substituents are present, their number is only limited by steric considerations, which depend upon the size of the substituent and of the substituted group; however, in general, from 1 to 3 substituents would be present.

Examples of such substituted groups which may be represented by $R^2$ or $R^4$ include the 2,2,2-trichloroethyl, 2-iodoethyl, 2-hydroxyethyl, 2,3-dihydroxypropyl, methoxymethyl, 2-methoxyethoxymethyl, p-methoxybenzyl, acetoxymethyl, 1-acetoxyethyl, pivaloyloxymethyl, phenacyl, methoxycarbonylmethyl, ethoxycarbonylmethyl, ethoxycarbonyloxymethyl, 1-(ethoxycarbonyloxy)ethyl, p-nitrobenzyl, 1-cyanoethyl, 2-cyanoethyl, methylthiomethyl, ethylthiomethyl, phenylthiomethyl, 2-methanesulfonylethyl, 2-benzenesulfonylethyl, (5-methyl-2-oxo-1,3-dioxolen-4-yl)methyl and (5-phenyl-2-oxo-1,3-dioxolen-4-yl)methyl groups.

We particularly prefer that $R^2$ should represent: a hydrogen atom; a straight or branched chain alkyl group having from 1 to 6 carbon atoms, for example a methyl, ethyl, propyl, isopropyl, butyl, isobutyl, pentyl or hexyl group; an aralkyl group, for example a benzyl group; or a protecting group which allows the protected carboxy group to be converted easily to a free carboxy group in the living body, for example an acetoxymethyl, pivaloyloxymethyl, phthalidyl, 1-(ethoxycarbonyloxy)ethyl or (5-methyl-2-oxo-1,3-dioxolen-4-yl)methyl group.

We also particularly prefer that $R^4$ should represent: a carboxy-protecting group of the type commonly used in organic synthesis, such as a t-butyl, methoxymethyl, 2,2,2-trichloroethyl, benzyl, p-methoxybenzyl or diphenylmethyl group; or a protecting group which allows the protected carboxy group to be converted easily to a free carboxy group in the living body, for example an acetoxymethyl, pivaloyloxymethyl, 1-(ethoxycarbonyloxy)ethyl, phthalidyl or (5-methyl-2-oxo-1,3-dioxolen-4-yl)methyl group.

Particularly preferred compounds of the invention are those compounds of formula (Ia) in which:

$R^2$ and $R^4$ are the most preferred groups defined above;

$R^1$—A— represents a straight or branched chain alkyl group having from 4 to 9 carbon atoms, for example a butyl, isobutyl, pentyl, isopentyl, neopentyl, hexyl, isooctyl, octyl or nonyl group; a cycloalkylethyl group in which the cycloalkyl part has 5 or 6 ring carbon atoms, for example a 2-cyclopentylethyl or 2-cyclohexylethyl group; an aralkyl group having a total of from 7 to 12 carbon atoms, for example a benzyl, phenethyl, 1-naphthylmethyl, 2-naphthylmethyl, 2-(1-naphthyl)ethyl or 2-(2-naphthyl)ethyl group; a phenoxymethyl group; a phenylthiomethyl group; a 2-(2-thienyl)ethyl group; a 2-(2-imidazolyl)ethyl group; or a 2-(2-thiazolyl)ethyl group;

$R^3$ represents a straight or branched chain alkyl group having from 1 to 6 carbon atoms, for example a methyl, ethyl, propyl, isopropyl, butyl, isobutyl, sec-butyl, t-butyl, pentyl or hexyl group; a cycloalkyl group having 5 or 6 ring carbon atoms, e.g. a cyclopentyl or cyclohexyl group; an aralkyl group having a total of from 7 to 11 carbon atoms, such as a benzyl or 1-naphthylmethyl group; an aryl group, such as a phenyl, p-fluorophenyl, 1-naphthyl or 2-naphthyl group; a heterocyclylmethyl group, such as a 2-imidazolylmethyl or 2-indolylmethyl group; or a heterocyclic group, such as a 2-thienyl, 3-thienyl, 2-furyl, 3-furyl, 2-thiazolyl, 2-pyridyl or 3-pyridyl group;

B represents a methylene group; and n is 2 or 3.

Still more preferred compounds are those in which:

$R^1$ represents a $C_4$-$C_7$ alkyl group, a $C_5$-$C_6$ cycloalkyl group, a phenyl group or a phenyl group having at least one substituent selected from the group consisting of substituents (a) and (b) defined above;

$R^2$ represents a hydrogen atom, a $C_1$-$C_4$ alkyl group or a benzyl group;

$R^3$ represents a $C_3$-$C_6$ alkyl group, a phenyl group or a phenyl group having at least one substituent selected from the group consisting of substituents (a) and (b) defined above;

$R^4$ represents a hydrogen atom, a $C_1$-$C_4$ alkyl group a benzyl group, a p-methoxybenzyl group or a diphenylmethyl group;

A represents a $C_1$ or $C_2$ alkylene group;

B represents a methylene group; and n is 2.

The most preferred compounds are those in which:

$R^1$ represents a butyl group, a pentyl group, a hexyl group, a cyclohexyl group or a phenyl group;

$R^2$ represents a hydrogen atom, a $C_2$-$C_4$ alkyl group, particularly an ethyl or butyl group or a benzyl group;

$R^3$ represents a phenyl group or a halophenyl group;

$R^4$ represents a hydrogen atom, a $C_2$-$C_4$ alkyl group, particularly a t-butyl group, a p-methoxybenzyl group or a diphenylmethyl group;

A represents an ethylene group;

B represents a methylene group; and n is 2.

Where the compounds of the invention contain one or two free carboxy groups, these compounds may also form salts with bases; the nature of the cation of the resulting salt is not critical to the present invention and, where the resulting compounds are for use as medicines, is only limited to the extent that the resulting salt must be pharmaceutically acceptable; where the compound is subsequently to be used as an intermediate for the production of another compound, even this restriction is not applicable. Of course, there are practical constraints, such as cost and availability of the bases used to form the salts, but these constraints vary from time to time and are irrelevant to the essence of the present invention. Examples of suitable salts include: alkali metal salts, for example sodium or potassium salts; alkaline earth metal salts, for example calcium or magnesium salts; other metal salts, for example aluminum salts; ammonium salts; salts with organic bases, for example triethylamine, dicyclohexylamine, cinchonine, guanidine or quinine salts; and salts with basic amino acids, for example lysine or arginine salts.

The compounds of the invention also contain an amino group which can potentially exert a basic effect and the compounds can thus also form acid addition salts. Where the compounds are to be used as medicines, the nature of such salts is only limited to the extent that the resulting compound should be pharmaceutically acceptable; where the compound is to be used as an intermediate, this criterion does not apply and any acid may be employed. Examples of suitable acids include inorganic acids, such as hydrogen halides, (for example hydrochloric acid or hydrobromic acid), sulfuric acid, phosphoric acid or nitric acid; organic carboxylic acids, for example oxalic acid, maleic acid, fumaric acid, tartaric acid or citric acid; and organic sulfonic acids, such as methanesulfonic acid or benzenesulfonic acid.

Specific examples of compounds of the invention are given in the following Table in which the definitions given relate to the foregoing formula (Ia). In this Table, the following abbreviations are employed:

Bu: butyl
iBu: isobutyl
tBu: t-butyl
Bz: benzyl
Dom: (5-methyl-2-oxo-1,3-dioxolen-4-yl)methyl
Et: ethyl
Etc: ethoxycarbonyl
Ety: ethylene (—$CH_2CH_2$—)
Fur: furyl
cHx: cyclohexyl
Me: methyl
Np: naphthyl
Oc: octyl
Ph: phenyl
Piv: pivaloyl
iPr: isopropyl
Thi: thienyl

TABLE

| Cpd No. | $R^1$—A | $R^2$ | $R^3$ | $R^4$ | B | n |
|---|---|---|---|---|---|---|
| 1 | 2-PhEt | H | Ph | H | $CH_2$ | 2 |
| 2 | 2-PhEt | Et | Ph | H | $CH_2$ | 2 |
| 3 | 2-PhEt | Bu | Ph | H | $CH_2$ | 2 |
| 4 | 2-PhEt | Bz | Ph | H | $CH_2$ | 2 |
| 5 | 2-PhEt | Et | Ph | tBu | $CH_2$ | 2 |
| 6 | 2-PhEt | Et | Ph | Bz | $CH_2$ | 2 |
| 7 | 2-PhEt | H | Me | H | $CH_2$ | 2 |
| 8 | 2-PhEt | Et | Me | H | $CH_2$ | 2 |
| 9 | 2-PhEt | Bu | Me | H | $CH_2$ | 2 |
| 10 | 2-PhEt | Bz | Me | H | $CH_2$ | 2 |
| 11 | 2-PhEt | Et | Me | tBu | $CH_2$ | 2 |
| 12 | 2-PhEt | H | iPr | H | $CH_2$ | 2 |
| 13 | 2-PhEt | Et | iPr | H | $CH_2$ | 2 |
| 14 | 2-PhEt | Bu | iPr | H | $CH_2$ | 2 |
| 15 | 2-PhEt | Bz | iPr | H | $CH_2$ | 2 |
| 16 | 2-PhEt | Et | iPr | tBu | $CH_2$ | 2 |
| 17 | 2-PhEt | H | 2-Thi | H | $CH_2$ | 2 |
| 18 | 2-PhEt | Et | 2-Thi | H | $CH_2$ | 2 |
| 19 | 2-PhEt | Bu | 2-Thi | H | $CH_2$ | 2 |
| 20 | 2-PhEt | Bz | 2-Thi | H | $CH_2$ | 2 |
| 21 | 2-PhEt | Et | 2-Thi | tBu | $CH_2$ | 2 |
| 22 | 2-PhEt | H | 3-Thi | H | $CH_2$ | 2 |
| 23 | 2-PhEt | Et | 3-Thi | H | $CH_2$ | 2 |
| 24 | 2-PhEt | Bu | 3-Thi | H | $CH_2$ | 2 |
| 25 | 2-PhEt | Bz | 3-Thi | H | $CH_2$ | 2 |
| 26 | 2-PhEt | Et | 3-Thi | tBu | $CH_2$ | 2 |
| 27 | 2-PhEt | H | 2-Fur | H | $CH_2$ | 2 |
| 28 | 2-PhEt | Et | 2-Fur | H | $CH_2$ | 2 |
| 29 | 2-PhEt | Bu | 2-Fur | H | $CH_2$ | 2 |
| 30 | 2-PhEt | Bz | 2-Fur | H | $CH_2$ | 2 |
| 31 | 2-PhEt | Et | 2-Fur | tBu | $CH_2$ | 2 |
| 32 | 2-PhEt | H | Bz | H | $CH_2$ | 2 |
| 33 | 2-PhEt | Et | Bz | H | $CH_2$ | 2 |
| 34 | 2-PhEt | Bu | Bz | H | $CH_2$ | 2 |
| 35 | 2-PhEt | Bz | Bz | H | $CH_2$ | 2 |
| 36 | 2-PhEt | Et | Bz | tBu | $CH_2$ | 2 |
| 37 | 2-PhEt | H | cHx | H | $CH_2$ | 2 |
| 38 | 2-PhEt | Et | cHx | H | $CH_2$ | 2 |
| 39 | 2-PhEt | Bu | cHx | H | $CH_2$ | 2 |
| 40 | 2-PhEt | Bz | cHx | H | $CH_2$ | 2 |
| 41 | 2-PhEt | Et | cHx | tBu | $CH_2$ | 2 |
| 42 | 2-cHxEt | H | Ph | H | $CH_2$ | 2 |
| 43 | 2-cHxEt | Et | Ph | H | $CH_2$ | 2 |
| 44 | 2-cHxEt | Bu | Ph | H | $CH_2$ | 2 |
| 45 | 2-cHxEt | Bz | Ph | H | $CH_2$ | 2 |

TABLE-continued

| Cpd No. | R¹—A | R² | R³ | R⁴ | B | n |
|---|---|---|---|---|---|---|
| 46 | 2-cHxEt | Et | Ph | tBu | CH₂ | 2 |
| 47 | Oc | H | Ph | H | CH₂ | 2 |
| 48 | Oc | Et | Ph | H | CH₂ | 2 |
| 49 | Oc | Bu | Ph | H | CH₂ | 2 |
| 50 | Oc | Bz | Ph | H | CH₂ | 2 |
| 51 | Oc | Et | Ph | tBu | CH₂ | 2 |
| 52 | iBu | H | Ph | H | CH₂ | 2 |
| 53 | iBu | Et | Ph | H | CH₂ | 2 |
| 54 | iBu | Bu | Ph | H | CH₂ | 2 |
| 55 | iBu | Bz | Ph | H | CH₂ | 2 |
| 56 | iBu | Et | Ph | Bz | CH₂ | 2 |
| 57 | 2-cHxEt | H | 2-Thi | H | CH₂ | 2 |
| 58 | 2-cHxEt | Et | 2-Thi | H | CH₂ | 2 |
| 59 | Oc | H | 2-Thi | H | CH₂ | 2 |
| 60 | Oc | Et | 2-Thi | H | CH₂ | 2 |
| 61 | iBu | H | 2-Thi | H | CH₂ | 2 |
| 62 | iBu | Et | 2-Thi | H | CH₂ | 2 |
| 63 | 2-PhEt | H | Ph | H | >CHMe | 2 |
| 64 | 2-PhEt | Et | Ph | H | >CHMe | 2 |
| 65 | 2-PhEt | H | Ph | H | Ety | 2 |
| 66 | 2-PhEt | Et | Ph | H | Ety | 2 |
| 67 | 2-PhEt | H | Ph | H | CH₂ | 3 |
| 68 | 2-PhEt | Et | Ph | H | CH₂ | 3 |
| 69 | 2-PhEt | Bu | Ph | H | CH₂ | 3 |
| 70 | 2-PhEt | Bz | Ph | H | CH₂ | 3 |
| 71 | 2-PhEt | Et | Ph | tBu | CH₂ | 3 |
| 72 | 2-PhEt | H | 2-Thi | H | CH₂ | 3 |
| 73 | 2-PhEt | Et | 2-Thi | H | CH₂ | 3 |
| 74 | 2-PhEt | Bu | 2-Thi | H | CH₂ | 3 |
| 75 | 2-PhEt | Bz | 2-Thi | H | CH₂ | 3 |
| 76 | 2-PhEt | Et | 2-Thi | tBu | CH₂ | 3 |
| 77 | 2-PhEt | H | Ph | H | CH₂ | 1 |
| 78 | 2-PhEt | Et | Ph | H | CH₂ | 1 |
| 79 | 2-PhEt | H | 2-Thi | H | CH₂ | 1 |
| 80 | 2-PhEt | Et | 2-Thi | H | CH₂ | 1 |
| 81 | 2-PhEt | Et | Ph | PivOMe | CH₂ | 2 |
| 82 | 2-PhEt | Et | Ph | 1-(EtcO)Et | CH₂ | 2 |
| 83 | 2-PhEt | Et | Ph | Dom | CH₂ | 2 |
| 84 | 2-PhEt | H | 4-FcHx | H | CH₂ | 2 |
| 85 | 2-PhEt | Et | 4-FcHx | H | CH₂ | 2 |
| 86 | 2-PhEt | Bu | 4-FcHx | H | CH₂ | 2 |
| 87 | 2-PhEt | Bz | 4-FcHx | H | CH₂ | 2 |
| 88 | 2-PhEt | H | 1-Np | H | CH₂ | 2 |
| 89 | 2-PhEt | Et | 1-Np | H | CH₂ | 2 |
| 90 | 2-PhEt | Bu | 1-Np | H | CH₂ | 2 |
| 91 | 2-PhEt | Bz | 1-Np | H | CH₂ | 2 |
| 92 | 2-PhEt | H | 2-Np | H | CH₂ | 2 |
| 93 | 2-PhEt | Et | 2-Np | H | CH₂ | 2 |
| 94 | 2-PhEt | Bu | 2-Np | H | CH₂ | 2 |
| 95 | 2-PhEt | Bz | 2-Np | H | CH₂ | 2 |
| 96 | 2-PhEt | Et | p-FPh | tBu | CH₂ | 2 |
| 97 | 2-PhEt | Bu | p-FPh | tBu | CH₂ | 2 |
| 98 | 2-PhEt | Bu | Ph | tBu | CH₂ | 2 |

Of the compounds listed above, preferred compounds from the point of view of their biological activity, are Compounds Nos. 1, 2, 3, 5, 84, 85, 86, 96, 97 and 98, Compounds Nos. 1, 2, 3, 84, 85 and 86 being most preferred.

The compounds of the present invention can contain many asymmetric carbon atoms and can thus exist in the form of many stereoisomers and the present invention envisages both the individual isolated isomers as well as mixtures thereof. The following carbon atoms are asymmetric in all of the compounds of the invention: the carbon atom to which the group represented by R¹—A— is attached; the carbon atom at the 3-position of the lactam ring; and the carbon atom to which the group represented by R³ is attached. In addition, depending upon the nature of the substituent groups on the compounds of the invention, other carbon atoms may also be asymmetric. The compounds of the invention may be prepared as mixtures of isomers and then separated by conventional techniques or they may be prepared by stereo-specific synthesis techniques, all of which are well-known to those skilled in the art.

The compounds of the present invention can be prepared by the condensation of a compound of formula (II):

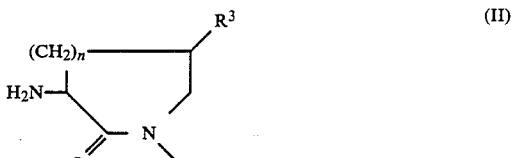

(in which R³, R⁴, B and n are as defined above) with a compound of formula (III):

$$R^1-A-CH(COOR^2)-X \qquad (III)$$

(in which R¹, R² and A are as defined above and X represents a halogen atom or a sulfonyloxy group) or by reductive condensation of the aforementioned compound of formula (II) with a compound of formula (IV):

$$R^1-A-C(=O)-COOR^2 \qquad (IV)$$

(in which R¹, R² and A are as defined above).

In the compound of formula (III), where X represents a halogen atom, this is preferably a chlorine, bromine or iodine atom; where X represents a sulfonyloxy group, this is preferably a substituted or unsubstituted C₁–C₆ alkanesulfonyloxy group, such as methanesulfonyloxy, ethanesulfonyloxy or trifluoromethanesulfonyloxy group, or a substituted or unsubstituted aromatic sulfonyloxy group, such as a benzenesulfonyloxy, p-toluenesulfonyloxy, p-nitrobenzenesulfonyloxy, o-nitrobenzenesulfonyloxy, m-nitrobenzenesulfonyloxy, 2,4-dinitrobenzenesulfonyloxy, 4-chloro-3-nitrobenzenesulfonyloxy, p-bromobenzenesulfonyloxy, p-chlorobenzenesulfonyloxy or 2,5-dichlorobenzenesulfonyloxy group; in the case of the substituted groups, substituents are selected from the group consisting of substituents (a) and (b) defined above.

Condensation of the compound of formula (II) with the compound of formula (III) is preferably effected in the presence of a solvent and of a base. The nature of the solvent is not critical, provided that it has no adverse effect upon the reaction; suitable solvents include: aliphatic and aromatic hydrocarbons, such as hexane or benzene; halogented aliphatic or aromatic, preferably aliphatic, hydrocarbons, such as methylene chloride or 1,2-dichloroethane; ethers, such as tetrahydrofuran or dioxane; esters, such as ethyl acetate; ketones, such as acetone; amides, such as dimethylformamide, dimethylacetamide, N-methyl-2-pyrrolidone or hexamethylphosphoric triamide; sulfoxides, such as dimethyl sulfoxide; and nitriles, such as acetonitrile. There is likewise no criticality as to the nature of the base to be employed, provided that it does not adversely affect the reaction. Suitable bases include, for example: alkali metal and alkaline earth metal carbonates, such as sodium carbonate, potassium carbonate or calcium carbonate; alkali metal bicarbonates, such as sodium bicarbonate or potassium bicarbonate; alkali metal hydrides, such as sodium hydride or lithium hydride; metal fluorides, such as potassium fluoride or cesium fluoride; and organic bases, such as triethylamine, pyridine, picoline or tetraethylammonium hydroxide. If desired, the reaction may be carried out in a two-phase reaction system employing water as the solvent for one phase and a water-immiscible solvent (such as methylene chloride or chloroform) for the other phase; in this case, a phase-transfer catalyst (such as tetrabutylammonium bromide or benzyltriethylammonium iodide) should be employed and the base may be a relatively strong base, such as an alkali metal hydroxide (for example sodium hydroxide or potassium hydroxide).

The reaction will take place over a wide range of temperatures and the precise temperature chosen is not critical to the present invention; we generally find it convenient to carry out the reaction at a temperature within the range from 0° to 120° C. The time required for the reaction will vary depending upon many factors, but primarily upon the natures of the solvent, base and reagents, and upon the reaction temperature, but a period of from 1 hour to 5 days will normally suffice.

After completion of the reaction, the desired compound may be obtained from the reaction mixture by conventional means. For example, one suitable recovery technique comprises: adding an organic solvent, such as ethyl acetate, to the reaction mixture; separating the organic layer and washing it with water; drying the organic layer; and distilling off the solvent to give the desired product. If necessary, this product can be further purified by various conventional techniques, such as recrystallization and/or the chromatography techniques, particularly column chromatography.

Reaction of the compound of formula (II) with the compound of formula (IV) takes place under reductive condensation conditions. The reductive conditions may be provided by a variety of means, for example: catalytic reduction using a metal, such as platinum, palladium, Raney nickel or rhodium, optionally on a carrier, in the presence of hydrogen; reduction with a metal hydride, such as lithium aluminum hydride, lithium borohydride, lithium cyanoborohydride, sodium cyanoborohydride, sodium borohydride or potassium borohydride; reduction with an active metal, such as sodium or magnesium, together with an alcohol, such as methanol or ethanol; or reduction with a metal, such as iron or zinc, and an acid, such as hydrochloric or acetic acid. The reaction is preferably effected in the presence of a solvent, the nature of which is not critical, provided that it has no adverse effect upon (although it may participate in) the reaction. Suitable solvents include water and a variety of organic solvents, for example: alcohols, such as methanol or ethanol; ethers, such as tetrahydrofuran, diethyl ether or dioxane; halogenated hydrocarbons, particularly halogenated aliphatic hydrocarbons, such as methylene chloride or chloroform; esters, such as ethyl acetate; aromatic hydrocarbons, such as benzene or toluene; amides, such as dimethylformamide or dimethylacetamide; and organic carboxylic acids, such as acetic acid. It will be noted that certain of the compounds mentioned herein as potential solvents may also serve as part of the reduction system described above and, in that case, the same compound may serve both as a reagent and as a solvent, if desired.

The reaction will take place over a wide range of temperatures, for example from $-20°$ C. to $+100°$ C., although the precise temperature chosen will depend upon several factors, of which the most important is the nature of the reductive system employed. The reaction can be carried out under atmospheric pressure, although, in some cases, it may be desirable to carry it out under an elevated or reduced pressure.

Of the compounds of formula (I), the monoester monocarboxylic acids in which $R^2$ represents an ester residue and $R^4$ represents a hydrogen atom and the dicarboxylic acids in which both $R^2$ and $R^4$ represent hydrogen atoms, as well as the salts of these acids, are medically the most important compounds. The monoester monocarboxylic acid can be prepared by selective deprotection of the ester residue represented by $R^4$ in a diester compound in which both $R^2$ and $R^4$ represent ester residues; alternatively, it may be prepared by the reductive condensation of an amino acid of formula (II) in which $R^4$ represents a hydrogen atom with a keto-ester of formula (IV) in which $R^2$ represents an ester residue.

A dicarboxylic acid of formula (I) in which both $R^2$ and $R^4$ represent hydrogen atoms can also be prepared by hydrolyzing a diester or monoester of formula (I) (in which $R^2$ and $R^4$ represent ester residues or $R^2$ represents an ester residue and $R^4$ represents a hydrogen atom) with an acid or base; it may also be prepared by reductive removal of the ester group or groups of the diester or monoester, or (when the compound contains an allyl ester group) catalytic removal of the allyl group with a suitable catalyst such as tetrakis(triphenylphosphine)palladium (O). The reaction conditions employed are the same as those described for deprotection of the carboxy-protecting group represented by $R^5$ in the compound of formula (V) described hereafter.

The starting materials of formula (II) employed in the processes of the present invention may be prepared in a variety of ways, for example, by the process illustrated in the following reaction scheme:

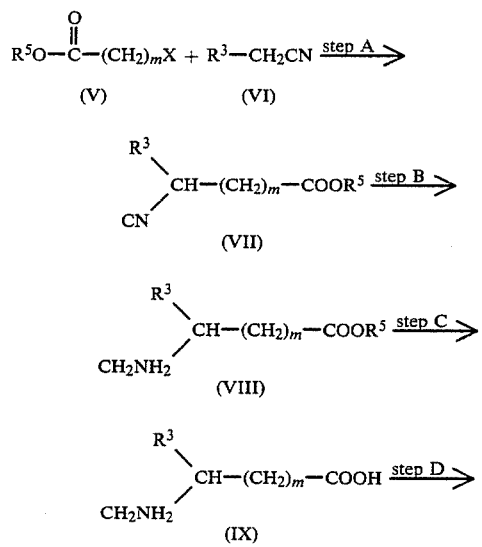

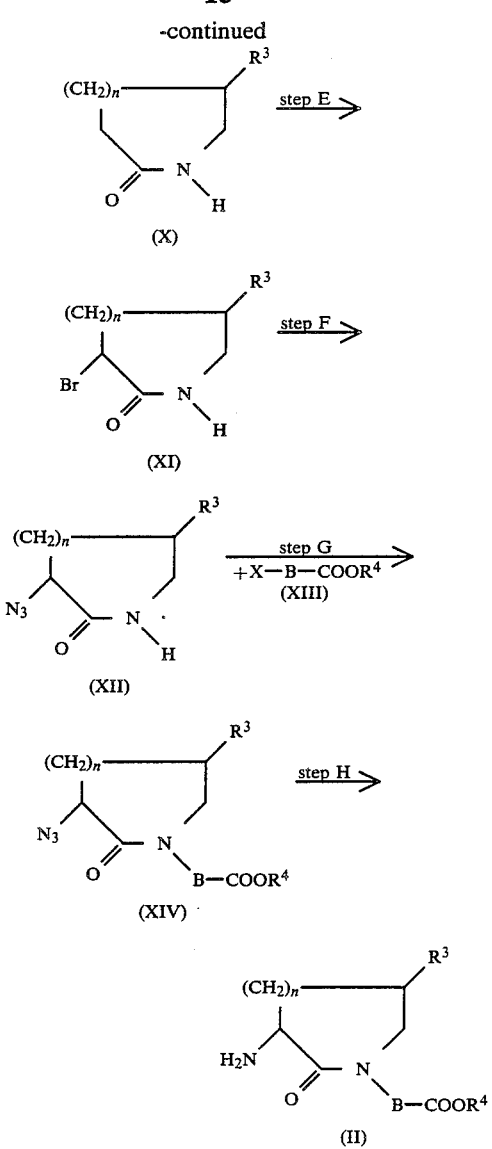

In the above formulae, $R^3$, $R^4$, B and n are as defined above. $m=(n+1)$ and $R^5$ represents a carboxy-protecting group.

The nature of the carboxy-protecting group represented by $R^5$ is not critical to the present invention, as its purpose is merely to protect the carboxy group from participation in the reaction of Steps A and B and it is then immediately eliminated in Step C. Accordingly, any protecting group known in the art for use in this type of reaction may be employed, normally an ester residue. Examples include: methyl and substituted methyl groups, such as the methyl, allyl, methoxymethyl, methylthiomethyl, 2-methoxyethoxymethyl, benzyloxymethyl, phenacyl, p-bromophenacyl or phthalimidomethyl groups; other lower (e.g. $C_2$-$C_6$, preferably $C_2$-$C_4$) alkyl groups, which may be substituted or unsubstituted, for example the ethyl, 2,2,2-trichloroethyl, 2-iodoethyl, 2-trimethylsilylethyl, 2-(p-toluenesulfonyl)ethyl or t-butyl groups; benzyl groups which may be substituted or unsubstituted, for example the benzyl, benzhydryl (i.e. diphenylmethyl), p-methoxybenzyl or p-nitrobenzyl groups; or silyl groups, preferably trialkylsilyl groups in which each alkyl part has from 1 to 6, preferably from 1 to 4, carbon atoms, for example the trimethylsilyl or t-butyldimethylsilyl groups. It should, however, be appreciated that these groups are given merely by way of exemplification and there is no limitation on the nature of the carboxy-protecting group, provided that it is capable of serving a protecting function.

In Step A of the reaction scheme, the acetonitrile derivative of formula (VI) is C-alkylated with the protected carboxyalkyl halide of formula (V). This reaction is preferably effected in the presence of a base and in a suitable solvent. The nature of the solvent employed is not critical, provided that it has no adverse effect upon the reaction. Examples of suitable solvents include: hydrocarbons, which may be aliphatic, cycloaliphatic or aromatic, such as hexane or benzene; halogenated hydrocarbons, particularly halogenated aliphatic hydrocarbons, such as methylene chloride; ethers, such as tetrahydrofuran or dioxane; esters, such as ethyl acetate; and amides, such as dimethylformamide, dimethylacetamide, N-methyl-2-pyrrolidone and hexamethylphosphoric triamide. There is likewise no criticality as to the nature of the base employed, provided that it does not interfere with the reaction. Suitable bases include: alkali metal hydrides, such as sodium hydride, lithium hydride or potassium hydride; alkyl-alkali metal compounds, such as butyllithium; alkali metal amides, such as lithium diisopropylamide, lithium dicyclohexylamide or lithium bis(trimethylsilyl)amide; alkali metal carbonates, such as sodium carbonate or potassium carbonate; and organic amines, such as triethylamine, triethylenediamine, 1,5-diazabicyclo[4.3.0]nonene-5 or 1,8-diazabicyclo[5.4.0]undecene-7. If desired, the reaction may be carried out in a two-phase reaction system, employing water as the solvent for one phase and a water-immiscible solvent (such as methylene chloride or chloroform) for the other phase; in this case, a phase-transfer catalyst (such as tetrabutylammonium bromide or benzyltriethylammonium iodide) should be employed, and the base may be a relatively strong base, such as an alkali metal hydroxide (for example sodium hydroxide or potassium hydroxide).

The reaction will take place over a wide range of temperatures and the precise temperature chosen is not critical to the present invention. In general, we find it convenient to carry out the reaction at a temperature within the range from $-20°$ C. to $+100°$ C. The time required for the reaction may vary widely, depending upon many factors, but notably upon the reaction temperature; at temperatures within the range suggested, a period of from 30 minutes to 24 hours will normally suffice.

After completion of the reaction, the desired compound may be recovered from the reaction mixture by conventional means. For example, one suitable recovery technique comprises: adding an organic solvent, such as ethyl acetate, to the reaction mixture; separating the organic layer and washing it with water; drying the organic layer; and distilling off the solvent to give the desired product. If necessary, this product can be further purified by various conventional techniques, such as recrystallization and/or the various chromatography techniques, notably column chromatography.

In Step B, the nitrile compound of formula (VII) is reduced to the corresponding aminomethyl compound of formula (VIII). This reaction may be carried out under similar conditions and employing similar reagents to those described in relation to the reductive condensation of the compound of formula (II) with the compound of formula (IV). After the reduction, the product of formula (VIII) can be purified by various known means, for example by recrystallization, the various chromatography techniques, such as column chromatography, or salt formation with an organic or inorganic acid.

In Step C, the carboxy-protecting group represented by $R^5$ is removed by conventional means well-known to those skilled in chemical synthesis and the particular reaction employed to remove this group is not critical to the present process. The precise removal reaction chosen will, of course, depend upon the precise nature of the carboxy-protecting group represented by $R^5$, for example:

where $R^5$ represents an alkyl group, such as a methyl or ethyl group, the compound may be deprotected by hydrolysis with an alkali, preferably an alkali metal hydroxide, such as lithium hydroxide, sodium hydroxide or potassium hydroxide;

where $R^5$ represents a protecting group such as a methoxymethyl, methoxyethoxymethyl, t-butyl, benzhydryl, p-methoxybenzyl, trimethylsilyl or t-butyldimethylsilyl group, the compound may be deprotected by reaction with an acid or a Lewis acid, such as hydrochloric acid, hydrobromic acid, trifluoroacetic acid or aluminum chloride;

where $R^5$ represents a group such as a benzyl or p-nitrobenzyl group, the compound may be deprotected by catalytic reduction, employing hydrogen in the presence of a suitable catalyst, for example palladium, which may be supported, for example, on carbon;

where $R^5$ represents a group such as a 2,2,2-trichloroethyl, 2-iodoethyl, phenacyl or p-bromophenacyl group, the compound may be deprotected by reduction employing a mixture of a metal powder (e.g. zinc powder) and an acid (e.g. acetic acid or hydrochloric acid); or where $R^5$ represents a group such as an allyl group, the compound may be deprotected by a catalytic reaction, employing, for example, tetrakis(triphenylphosphine)palladium (O).

The reaction in this deprotection Step C is preferably effected in the presence of a solvent, the nature of which is not critical, provided that it has no adverse effect upon the reaction. The optimum solvent will, of course, depend upon the precise reaction chosen and, as is obvious to those skilled in the art, in some cases, the solvent may participate in the deprotection reaction. In general terms, suitable solvents may be chosen from the class consisting of: water; acids, preferably organic carboxylic and more preferably aliphatic carboxylic, acids such as acetic acid or formic acid; alcohols, such as methanol or ethanol; ethers, such as tetrahydrofuran, dioxane or anisole; ketones, such as acetone; halogenated hydrocarbons, preferably halogenated aliphatic hydrocarbons, such as methylene chloride or chloroform; and hydrocarbons, which may be aliphatic or aromatic, preferably aromatic, such as benzene or toluene. These reactions will take place over a wide range of temperatures, for example at a temperature within the range from $-10°$ C. to $+100°$ C.; in general, the time allowed for the reaction will vary depending upon the nature of the deprotection reaction and other reaction conditions, including the reaction temperature; at one extreme, a relatively fast reaction will be complete within perhaps 30 minutes, whereas, at the other extreme, it may be advisable to allow 24 hours for the reaction: however, these are matters well within the skill and knowledge of the laboratory technician.

If desired, the compound of formula (IX) may be purified by various conventional means, for example by isoelectric precipitation, recrystallization or the various chromatography techniques, such as column chromatography.

However, if purification of the compound of formula (IV) is troublesome, the amino acid compound of formula (IX) can be prepared by the alternative reaction sequence shown below:

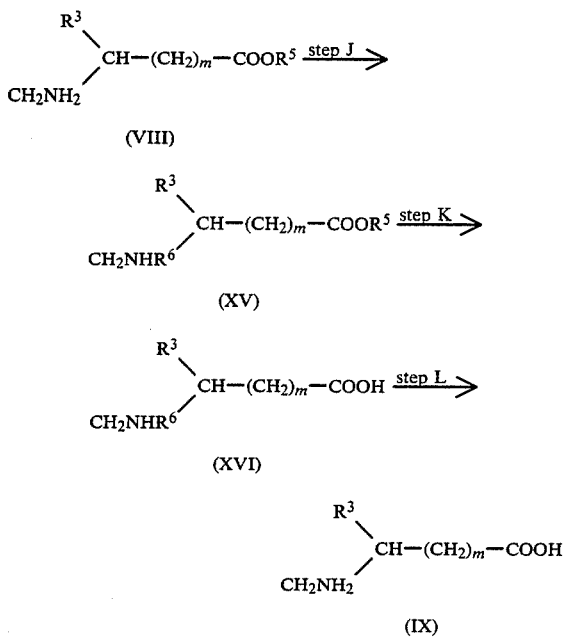

In these formulae, $R^3$, $R^5$ and m are as defined above and $R^6$ represents an amino-protecting group.

There is no criticality as to the nature of the amino-protecting group represented by $R^6$ as this group is removed in the course of the reaction and thus does not appear in the final product. Accordingly, it has no influence on the nature of the final product and may be chosen having regard solely to its protecting function. Examples of such protecting groups include: alkoxycarbonyl groups, in which the alkoxy part preferably has from 1 to 6, more preferably from 1 to 4, carbon atoms and which may be substituted or unsubstituted [examples of substituents being any of those groups and atoms listed above as substituents (a) and (b) as well as lower (e.g. $C_1$-$C_4$) alkylidene groups], for example the 2,2,2-trichloroethoxycarbonyl, 2-iodoethoxycarbonyl, 2-(p-toluenesulfonyl)ethoxycarbonyl, trimethylsilylethoxycarbonyl, t-butoxycarbonyl, allyloxycarbonyl, benzyloxycarbonyl, p-methoxybenzyloxycarbonyl or p-nitrobenzyloxycarbonyl groups; $C_1$-$C_7$ aliphatic carboxylic acyl or ($C_6$-$C_{10}$ carbocyclic aryl) carboxylic acyl groups, which may be unsubstituted or have one or more of the substituents listed in groups (a) and (b) above, for example the formyl, acetyl, benzoyl, chloroacetyl or trifluoroacetyl groups; cyclic diacyl groups, such as the phthaloyl or 2,3-diphenylmalonyl groups; substituted methyl groups, such as the methoxymethyl, benzyloxymethyl, benzyl, 3,4-dimethoxybenzyl or trityl groups; alkylidene or aralkylidene groups, such as the isopropylidene, benzylidene or salicylidene groups; acylvinyl groups, such as the 2-acetyl-1-methylvinyl or 2-benzoyl-1-methylvinyl groups; and silyl groups, particularly trialkylsilyl groups in which each alkyl part has from 1 to 6, preferably from 1 to 4, carbon atoms, for example the trimethylsilyl or t-butyldimethylsilyl groups. It should, however, be appreciated that these groups are given by way of example only and that the nature of the group is not critical, provided that it serves its required protecting function.

In Step J of this route, the amino group in the compound of formula (VIII) is first protected by conventional means to give the compound of formula (XV). Then, in Step K, the carboxy-protecting group represented by $R^5$ is removed by the appropriate one of the reactions described above. Finally, in Step L, the amino-protecting group represented by $R^6$ is removed by conventional means to prepare the amino acid compound of formula (IX). This route is particularly advantageous if the compound of formula (XV) crystallizes easily and so may be purified without difficulty.

In Step D, the compound of formula (IX) is cyclized to form a corresponding lactam of formula (X) by condensing the free amino group with the free carboxy group, to form an amide linkage, of a type which is well-known in the field of peptide chemistry. This reaction may generally be carried out by contacting the compound of formula (IX) with a dehydrating agent, such as N,N'-dicyclohexylcarbodiimide, carbonyldiimidazole, diphenylphosphoryl azide, diethyl cyanophosphate or phosphorus pentachloride. If a dehydrating agent of the carbodiimide type is employed, the reaction can be accelerated by carrying out the reaction in the presence of 1-hydroxybenzotriazole, N-hydroxysuccinimide or a similar compound. It may also be advantageous to carry out the reaction in the presence of a base, which may be an organic base, for example pyridine, picoline, triethylamine or N-methylmorpholine, or an inorganic base, such as sodium carbonate or sodium bicarbonate. The reaction is preferably effected in the presence of a solvent, the nature of which is not critical, provided that it has no adverse effect upon the reaction. Suitable solvents include, for example: amides, such as dimethylformamide, hexamethylphosphoric triamide, N-methyl-2-pyrrolidone or dimethylacetamide; ethers, such as tetrahydrofuran or dioxane; nitriles, such as acetonitrile; lower alcohols, such as methanol or ethanol; ketones, such as acetone; halogenated hydrocarbons, preferably aliphatic hydrocarbons, such as methylene chloride or chloroform; esters, such as ethyl acetate; or aromatic hydrocarbons, such as benzene or toluene. Sometimes, the product can be isolated as crystals from the reaction mixture; at other times, other recovery techniques (such as those described elsewhere in the specification) may be employed; if desired, the product can be purified by various conventional techniques, such as the chromatography techniques, especially column chromatography.

In Step E, the compound of formula (X) is brominated, to introduce a bromine atom at the 3-position of the lactam derivative (X). This may, for example, be carried out using phosphorus pentachloride and bromine according to the method reported by Nagasawa et al [Journal of Medicinal Chemistry 14, 501 (1971)].

In Step F, the resulting compound of formula (XI) is reacted with an azide to convert the bromine atom to an azido group in the compound of formula (XII). The azide is preferably an alkali metal azide, such as sodium azide or lithium azide. The reaction is preferably effected in the presence of a solvent, the nature of which is not critical, provided that it has no adverse effect upon the reaction. Examples of suitable solvents include: amides, such as dimethylformamide, dimethylacetamide or N-methyl-2-pyrrolidone; ethers, such as tetrahydrofuran or dioxane; ketones, such as acetone; and nitriles, such as acetonitrile. The reaction will take place over a wide range of temperatures and the precise temperature chosen is not critical to the reaction. We generally find it convenient to carry out the reaction at a temperature in the range from room temperature to 100° C. The time required for the reaction may vary widely, depending upon many factors, notably the reaction temperature; however, at the temperatures suggested above, a period of from 1 to 24 hours will normally suffice. The desired compound of formula (XII) can then be obtained from the reaction system by, for example, extracting it with a solvent (such as ethyl acetate), washing the extract with water and then distilling off the organic solvent. If necessary, the product can be purified by conventional means, particularly the various chromatography techniques, such as column chromatography.

In Step G of the reaction scheme, the compound of formula (XIV) can be prepared by N-alkylation of the compound of formula (XII), employing a compound of formula (XIII):

$$X-B-COOR^4 \qquad (XIII)$$

[in which B and $R^4$ are as defined above and X represents a halogen atom or a sulfonyloxy group, examples of which are given in relation to the atom or group represented by X in the compound of formula (III), preferably a bromine atom]. The reaction may be effected under the same conditions and employing the same reagents as described above in relation to Step A. The desired compound of formula (XIV) may be recovered from the reaction mixture by conventional means. For example, one suitable recovery technique comprises: adding an organic solvent, such as ethyl acetate, to the reaction mixture; separating the organic layer and washing it with water; drying the organic layer; and then finally distilling off the solvent to give the desired compound. If necessary, this compound may be further purified by such conventional means as the various chromatography techniques, particularly column chromatography.

In Step H, the azido group is reduced to an amino group by any method well-known in the field of organic synthesis. Examples of suitable reactions include:

catalytic reduction in the presence of hydrogen, using, as catalyst, a metal, such as palladium, platinum or Raney nickel, on a suitable catalyst, for example carbon in an appropriate form;

reduction with a metal hydride, such as sodium borohydride; or reduction by reaction with a thiol, such as 1,3-propanedithiol.

The reduction reaction is normally effected in the presence of a solvent, the nature of which is not critical, provided that it has no adverse effect upon the reaction. Suitable solvents include, for example: alcohols, such as methanol or ethanol; ethers, such as tetrahydrofuran, diethyl ether or dioxane; halogenated hydrocarbons, particularly halogenated aliphatic hydrocarbons, such as methylene chloride or chloroform; esters, such as ethyl acetate; hydrocarbons, particularly aromatic hydrocarbons, such as benzene or toluene; amides, such as dimethylformamide or dimethylacetamide; lower fatty acids, such as acetic acid; and water. The reaction will take place over a wide range of temperatures and the particular temperature chosen is not critical. We generally find it convenient to carry out the reaction at a temperature in the range from −20° C. to +100° C. After completion of the reaction, the product may, if required, be further purified by conventional techniques, such as column chromatography or salt formation with an organic or inorganic acid.

In the compounds of formulae (II), (XII) and (XIV), the carbon atom to which the amino group or the azido group is attached and the carbon atom to which the group represented by $R^3$ is attached are both asymmetric carbon atoms. Hence, two kinds of isomers can exist in the racemate of each of these compounds: one isomer in which the amino or azido group and $R^3$ are in the same orientation (the cis configuration); and the other isomer in which these groups are in the opposite orientation (the trans configuration). If necessary, these diastereoisomers may be separated by chromatography or fractional recrystallization. Furthermore, when such compounds containing amino or carboxy groups as the compounds (II), (VII) and (IX) are racemic, the mixture of optical isomers may be separated by conventional resolution methods, for example the formation of salts with optically active bases, such as cinchonine, cinchonidine, quinine or quinidine, or with optically active organic acids, e.g. l-camphorsulfonic acid or d-camphorsulfonic acid. Optical isomers can also be resolved by other known techniques, including various kinds of chromatography, fractional crystallization etc.

As noted above, the compounds of the present invention have the ability to inhibit the activity of ACE, the enzyme which converts angiotensin I to angiotensin II and also inactivates bradykinin. The physiological activity of the compounds of the invention can be evaluated by determining the concentration of the test compound required to inhibit the activity of ACE by 50% in vitro ($IC_{50}$), for example by the procedure of D. W. Cushman et al. [Biochemical Pharmacology, 20, 1637 (1971)]. Specifically, solutions of ACE extracted from rabbit lungs and, as substrate, hippurylhistidylleucine, to which had been added the test compound at various concentrations, were added to a borate buffer solution containing sodium chloride, and the pH was adjusted to a value of 8.3. The enzymatic reaction was allowed to proceed at 37° C. for 30 minutes, after which time the reaction was terminated by adding 1N aqueous hydrochloric acid. The hippuric acid formed by this reaction was extracted with ethyl acetate and the solvent was then distilled from the extract. The residual hippuric acid was dissolved in water. The amount of hippuric acid in the resulting aqueous solution was determined by the absorbency to ultraviolet radiation at 228 nm. The resulting values were then plotted to form a curve indicating the relationship between the amount of hippuric acid formed and the concentration of the test compound. The $IC_{50}$ value can be obtained by reading on this curve the concentration of the test compound which reduces the amount of hippuric acid formed to one half of that formed when no test compound is present. The $IC_{50}$ values obtained for various of the compounds of the invention by this procedure are shown in the following Table. The compounds tested were as follows:

A: α-{3(S)-[1(S)-carboxy-3-phenylpropylamino]-2-oxo-6(R)-phenylperhydroazepin-1-yl}acetic acid (Isomer A-2, product of Example 4);

B: α-{3(S)-[1(S)-carboxy-3-phenylpropylamino]-2-oxo-6(S)-phenylperhydroazepin-1-yl}acetic acid (Isomer B-2, product of Example 5).

C: α-{3(S)-[1(S)-carboxy-3-phenylpropylamino]-6(R)-(p-fluorophenyl)-2-oxoperhydroazepin-1-yl}acetic acid (product of Example 8).

TABLE

| Test Compound | $IC_{50}$ (moles/liter) |
| --- | --- |
| A | $1.4 \times 10^{-9}$ |
| B | $2.0 \times 10^{-9}$ |
| C | $1.7 \times 10^{-9}$ |

As can be clearly seen from the results in the above Table, the compounds of the invention inhibit ACE activity at very low concentrations and are thus useful as diagnostic, preventative and therapeutic agents for hypertensive patients; likewise, salts of these compounds would have similar activities.

In addition, the compounds of Examples 2, 3, 7, 10 and 12 were tested in vivo. Each of these test compounds was administered orally to rats and its inhibitory effect on angiotensin I-induced hypertension was determined. These compounds all showed strong and lasting inhibitory effects.

For practical, therapeutic use, the compounds of the invention are preferably administered in combination with suitable pharmaceutically acceptable carriers, vehicles or diluents. The compounds can be administered orally or non-orally (e.g. parenterally by intravenous or intramuscular injection) and the form of the composition will, of course, be determined by the intended route of administration. For oral administration, the compounds of the invention may, for example, be administered as powders, granules, tablets, capsules, syrups or elixirs. For parenteral administration, the compounds will be administered in the form of a suitable injectable composition, in which the compound of the invention is dissolved or suspended in a pyrogen-free injectable medium. The dose will vary depending upon the nature and severity of the disorder, as well as upon the age, condition and body weight of the patient. For example, for the therapy of an adult human patient, the dose at each administration would preferably be from 0.5 to 1000 mg, more preferably from 1 to 100 mg. for oral administration, whilst the preferred dose at each administration for intravenous injection is from 0.1 to 100 mg, more preferably from 0.2 to 10 mg. One or more of these doses, preferably from 1 to 3 doses, may be administered daily.

The invention is further illustrated by the following Examples, which describe the preparation of various compounds of the invention, including separation and/or preparation of individual isomers thereof. The values for optical rotation were all measured with the sodium D-line, i.e. all values are $[\alpha]_D$.

EXAMPLE 1 t-Butyl α-{3-[1(S)-ethoxycarbonyl-3-phenylpropylamino]-2-oxo-6-phenylperhydroazepin-1-yl}acetate (Compound No. 5)

1(a) Ethyl 5-cyano-5-phenylvalerate 5 g of sodium hydride (as a 55% w/w dispersion in mineral oil) were added slowly to a solution of 11.7 g of phenylacetonitrile and 19.5 g of ethyl 4-bromobutyrate in 150 ml of dimethylformamide, and the reaction mixture was stirred for 4 hours at room temperature. It was then dissolved in ethyl acetate and water. The ethyl acetate layer was separated, washed with an aqueous solution of potassium bisulfate and then with an aqueous solution of sodium chloride, dried over anhydrous magnesium sulfate and concentrated by evaporation under reduced pressure. The oily residue was subjected to silica gel column chromatography using a 1:4 by volume mixture of ethyl acetate and cyclohexane as eluent, to give 13.5 g of the title compound as a colorless liquid.

Nuclear Magnetic Resonance Spectrum (CDCl$_3$) δ ppm: 1.22 (3H, triplet, J=7 Hz); 1.7–2.1 (4H, multiplet); 2.22–2.5 (2H, multiplet); 3.7–4.0 (1H, multiplet); 4.12 (2H, quartet, J=7 Hz); 7.33 (5H, singlet).

1(b) Ethyl 6-(t-butoxycarbonylamino)-5-phenylhexanoate

About 10 ml of Raney nickel were added to a solution of 58 g of ethyl 5-cyano-5-phenylvalerate [prepared as described in step (a) above] in 400 ml of ethanol, and the mixture was stirred for 2.5 hours at 40° C., under a hydrogen pressure of 3 kg/cm$^2$. The catalyst was filtered off and the filtrate was condensed to give ethyl 6-amino-5-phenylhexanoate as an oily substance. The whole of this oily substance was dissolved in 300 ml of methylene chloride, and 40 ml of triethylamine were added to the mixture. 55 g of di-t-buty pyrocarbonate were added to this solution in an ice-bath. The mixture was stirred for 1 hour, and then the solvent was evaporated off under reduced pressure. The residue was dissolved in ethyl acetate and water. The ethyl acetate layer was separated and washed with an aqueous solution of potassium bicarbonate and then with an aqueous solution of sodium chloride. It was then dried over anhydrous magnesium sulfate and the solvent was distilled off under reduced pressure. The residual syrup was mixed with cyclohexane and allowed to stand. The crystals which separated out were collected by filtration as the title product, yield 25 g. The filtrate was condensed and subjected to silica gel column chromatography using a 1:5 by volume mixture of ethyl acetate and cyclohexane as eluent, to give a further 20.5 g of the title compound as crystals, melting at 82°–84° C. Total yield 45.5 g.

Nuclear Magnetic Resonance Spectrum (CDCl$_3$) δ ppm: 1.22 (3H, triplet, J=7 Hz); 1.42 (9H, singlet); 1.45–1.75 (4H, multiplet); 2.1–2.4 (2H, multiplet); 2.55–3.75 (3H, multiplet); 4.18 (2H, quartet, J=7 Hz); 4.35 (1H, multiplet); 7.0–7.4 (5H, multiplet).

1(c) 6-Amino-5-phenylhexanoic acid hydrochloride

To 370 ml of an ethanolic suspension containing 37.0 g of ethyl 6-(t-butoxycarbonylamino)-5-phenylhexanoate [prepared as described in step (b) above] were added 79 ml of water containing 8.8 g of sodium hydroxide. The reaction mixture was stirred for 1 hour at room temperature and then the solvent was distilled off under reduced pressure. The residue was mixed with ethyl acetate and water, and the aqueous layer was adjusted to a pH value of 3 by the addition of concentrated hydrochloric acid. The ethyl acetate layer was separated, washed with water and dried over anhydrous magnesium sulfate. Evaporation of the solvent gave quantitatively 6-(t-butoxycarbonylamino)-5-phenylhexanoic acid as a syrupy substance.

Nuclear Magnetic Resonance Spectrum (CDCl$_3$) δ ppm: 1.39 (9H, singlet); 1.45–1.9 (4H, multiplet); 2.1–2.45 (2H, multiplet); 2.5–3.7 (3H, multiplet); 4.46 (1H, multiplet); 7.0–7.4 (5H, multiplet).

The whole of this syrup was dissolved in 100 ml of a 4N solution of hydrogen chloride in dioxane. The mixture was stirred for 16 hours and then diethyl ether was added to it. The crystals which separated out were collected by filtration to give 27.5 g of the title compound, melting at 163°–165.5° C.

Nuclear Magnetic Resonance Spectrum [(CD$_3$)$_2$SO] δppm: 1.1–1.8 (4H, multiplet); 2.17 (2H, triplet, J=7 Hz); 2.8–3.3 (3H, multiplet); 7.1–7.5 (5H, multiplet).

1(d) 6-Phenylperhydroazepin-2-one 27.6 ml of diphenylphosphoryl azide and then 37.5 ml of N-methylmorpholine were added to 260 ml of dimethylformamide containing 26.0 g of 6-amino-5-phenylhexanoic acid hydrochloride [prepared as described in step (c) above] in an ice-bath. The reaction mixture was stirred for 3.5 hours at room temperature, and then dissolved in 0.5 liter of ethyl acetate and 0.5 liter of water. The ethyl acetate layer was separated, washed with water and dried over anhydrous magnesium sulfate. The solvent was distilled off and the residue was subjected to silica gel column chromatography using a 2:1 by volume mixture of ethyl acetate and methylene chloride as eluent, to give 4.0 g of the title compound as crystals, melting at 153.5°–154.5° C. (with decomposition).

Nuclear Magnetic Resonance Spectrum (CDCl$_3$) δ ppm: 1.4–2.3 (4H, multiplet); 2.4–2.9 (2H, multiplet); 3.1–3.8 (3H, multiplet); 6.6 (1H, multiplet); 7.0–7.5 (5H, multiplet).

1(e) 3-Bromo-6-phenylperhydroazepin-2-one 4.4 g of phosphorus pentachloride were added slowly to 60 ml of methylene chloride containing 4.0 g of 6-phenylperhydroazepin-2-one [prepared as described in step (d) above], under a stream of nitrogen, keeping the temperature of the reaction solution at 0° to 5° C. After this addition, the reaction mixture was stirred for 20 minutes, and then 40 mg of iodine, followed by 21.1 ml of a 1M methylene chloride solution of bromine, were dropped into it at 0°–5° C. When this addition was complete, the reaction mixture was stirred for 1 hour. The volume of reaction mixture was reduced by half by evaporation under reduced pressure, to separate the title compound as crystals. After the addition of water, the separated crystals were collected by filtration and washed with ethyl acetate, to give 1.8 g of an isomer of the title compound, melting at 218°–219.5° C.

This compound is named "Isomer A".

Nuclear Magnetic Resonance Spectrum [(CD$_3$)$_2$SO] δ ppm: 1.7–2.25 (4H, multiplet); 2.5–4.0 (3H, multiplet); 4.7 (1H, multiplet); 7.26 (5H, singlet); 7.9 (1H, multiplet).

The filtrate was diluted with methylene chloride, washed with an aqueous solution of sodium thiosulfate and dried over anhydrous magnesium sulfate. The solvent was evaporated and the crystals which separated were collected by filtration and washed with methylene chloride to give 1.1 g of crystals. This product is a mixture of Isomer A and Isomer B.

The resulting filtrate was concentrated further to give 2.6 g of a crystalline substance rich in Isomer B.

1(f) 3(S*)-Azido-6(R*)-phenylperhydroazepin-2-one (Isomer A)

2.0 g of sodium azide were added to 20 ml of dimethylformamide containing 1.6 g of 3-bromo-6-phenylperhydroazepin-2-one (Isomer A) [prepared as described in step (e) above]. The mixture was stirred for 6 hours at 60° C. and then diluted with ethyl acetate, washed with water three times and dried over anhydrous magnesium sulfate. The solvent was then distilled off. The crystalline residue was triturated in a 1:1 by volume mixture of methylene chloride and diisopropyl ether and then collected by filtration, to give 1.14 g of the title compound melting at 150°–152° C. (with decomposition).

Thin layer chromatography on silica gel (developing solvent ethyl acetate-methylene chloride, 1:2 by volume) Rf value=0.69.

Infrared Absorption Spectrum (Nujol-trade mark-mull) $\nu_{max}$cm$^{-1}$: 3230, 2100, 1670.

Nuclear Magnetic Resonance Spectrum (CDCl$_3$) δ ppm: 1.6–2.2 (4H, multiplet); 2.4–3.0 (1H, multiplet); 3.0–4.4 (3H, multiplet); 7.0–7.4 (5H, multiplet); 7.73 (1H, multiplet).

1(g) 3(S*)-Azido-6(S*)-phenylperhydroazepin-2-one (Isomer B)

Using a similar procedure to that described in Example 1(f), 2.6 g of the crystals rich in Isomer B of 3-bromo-6-phenylperhydroazepin-2-one [prepared from the final filtrate of Example 1(e)] afforded a crude product from which 0.97 g of the title compound was obtained through silica gel column chromatography using a 2:1 by volume mixture of methylene chloride and ethyl acetate as eluent.

Melting point: 122°–125° C. (with decomposition).

Thin layer chromatography on silica gel (developing solvent ethyl acetate-methylene chloride, 1:2 by volume) Rf value=0.63.

Infrared Absorption Spectrum (Nujol mull) $\nu_{max}$cm$^{-1}$: 3220, 2110, 1675.

Nuclear Magnetic Resonance Spectrum [(CD$_3$)$_2$SO] δ ppm: 1.75–2.2 (4H, multiplet); 2.4–3.7 (3H, multiplet); 4.35–4.55 (1H, multiplet); 7.1–7.4 (5H, multiplet); 7.96 (1H, multiplet).

1(h) t-Butyl α-[3(S*)-azido-2-oxo-6(R*)-phenylperhydroazepin-1-yl]acetate (Isomer A)

0.9 ml of t-butyl bromoacetate followed by 219 mg of sodium hydride (as a 55% w/w dispersion in mineral oil) were added, under a stream of nitrogen, to a solution of 1.05 g of 3(S*)-azido-6(R*)-phenylperhydroazepin-2-one (Isomer A) [prepared as described in Example 1(f)] in 10 ml of dimethylformamide, whilst ice-cooling. The mixture was stirred for 1.5 hours, and then ethyl acetate and water were added. The ethyl acetate layer was separated, washed with water, and dried over anhydrous magnesium sulfate. The solvent was then distilled off. The residue was purified by silica gel column chromatography using a 1:4 by volume mixture of ethyl acetate and cyclohexane as eluent, to give 1.54 g of the title compound as crystals, melting at 119°–121° C.

Infrared Absorption Spectrum (Nujol mull) $\nu_{max}$cm$^{-1}$: 2130, 1750, 1660.

Nuclear Magnetic Resonance Spectrum (CDCl$_3$) δ ppm: 1.47 (9H, singlet); 1.8–2.3 (4H, multiplet); 2.8–4.6 (4H, multiplet); 4.11 (2H, AB-quartet, Δδ=0.33 ppm, J=17 Hz); 7.0–7.5 (5H, multiplet).

1(i) t-Butyl α-[3(S*)-azido-2-oxo-6(S*)-phenylperhydroazepin-1-yl]acetate (Isomer B)

Using a similar procedure to that described in Example 1(h), 1.21 g of 3(S*)-azido-6(S*)-phenylperhydroazepin-2-one (Isomer B) [prepared as described in Example 1(g)], 1 ml of t-butyl bromoacetate and 252 mg of sodium hydride (as a 55% w/w dispersion in mineral oil) afforded 1.9 g of the title compound as a syrup.

Infrared Absorption Spectrum (liquid film) $\nu_{max}$cm$^{-1}$: 2120, 1740, 1660.

Nuclear Magnetic Resonance Spectrum (CDCl$_3$) δ ppm: 1.46 (9H, singlet); 1.8–2.3 (4H, multiplet); 2.8–4.6 (4H, multiplet); 3.98 (2H, AB-quartet, Δδ=0.5 ppm, J=17 Hz); 7.0–7.5 (5H, multiplet).

1(j) t-Butyl α-[3(S*)-amino-2-oxo-6(R*)-phenylperhydroazepin-1-yl]acetate (Isomer A)

0.3 g of 5% w/w palladium-on-carbon was added to 30 ml of ethanol containing 1.4 g of t-butyl α-[3(S*)-azido-2-oxo-6(R*)-phenylperhydroazepin-1-yl]acetate (Isomer A) [prepared as described in Example 1(h)], and under one atmosphere pressure of hydrogen the reaction mixture was shaken for 4 hours at 40° C. The catalyst was filtered off and the solvent was evaporated under reduced pressure, to give 1.56 g of the title compound as a gummy substance.

Nuclear Magnetic Resonance Spectrum (CDCl$_3$) δ ppm: 1.47 (9H, singlet); 1.5–2.3 (6H, multiplet); 2.7–4.2 (4H, multiplet); 4.10 (2H, singlet); 7.0–7.5 (5H, multiplet).

1(k) t-Butyl α-[3(S*)-amino-2-oxo-6(S*)-phenylperhydroazepin-1-yl]acetate (Isomer B)

Reduction of 1.9 g of t-butyl α-[3(S*)-azido-2-oxo-6(S*)-phenylperhydroazepin-1-yl]acetate (Isomer B) [prepared as described in Example 1(i)] with 5% w/w palladium-on-carbon in a similar manner to that described in Example 1(j) gave 1.8 g of the title compound as a gummy substance.

Nuclear Magnetic Resonance Spectrum (CDCl$_3$) δ ppm: 1.43 and 1.46 (together 9H, each singlet); 1.7–2.3 (4H, multiplet); 2.8–4.5 (6H, multiplet); 3.32 (2H, broad singlet); 7.0–7.4 (5H, multiplet).

1(l) t-Butyl α-{3-[1(S)-ethoxycarbonyl-3-phenylpropylamino]-2-oxo-6-phenylperhydroazepin-1-yl}acetate (Isomer A-1 and Isomer A-2 of Compound No. 5)

0.73 ml of triethylamine followed by 1.80 g of ethyl 4-phenyl-2(R)-trifluoromethanesulfonyloxybutyrate were added to a solution of 1.56 g of t-butyl α-[3(S*)-amino-2-oxo-6(R*)-phenylperhydroazepin-1-yl]acetate (Isomer A) [prepared as described in Example 1(j)] in 20 ml of methylene chloride, in an ice-bath. The reaction solution was allowed to stand for 16 hours at room temperature and then concentrated by evaporation under reduced pressure. The residue was dissolved in ethyl acetate. The solution was washed with water and dried over anhydrous magnesium sulfate, and then the solvent was distilled off. The residue was purified by silica gel column chromatography using a 3:1 by volume mixture of cyclohexane and ethyl acetate as eluent, to give two isomers separately.

The isomer first eluted (Isomer A-1) was a syrup, yield 0.84 g, and has been identified as t-butyl α-{3(R)-[1(S)-ethoxycarbonyl-3-phenylpropylamino]-2-oxo-6(S)-phenylperhydroazepin-1-yl}acetate.

$[\alpha]^{25}$ −45.3° (C=1, dimethylformamide).

Thin layer chromatography on silica gel (developing solvent cyclohexane-ethyl acetate, 3:1 by volume) Rf value=0.49.

Nuclear Magnetic Resonance Spectrum (CDCl$_3$) δ ppm: 1.24 (3H, triplet, J=7 Hz); 1.46 (9H, singlet); 1.6–2.3 (7H, multiplet); 2.6–4.0 (7H, multiplet); 4.04 (2H, AB-quartet, Δδ=0.40 ppm, J=18 Hz); 4.14 (2H, quartet, J=7 Hz); 7.0–7.4 (10H, multiplet).

The isomer next eluted (Isomer A-2) was a syrup, yield 0.95 g, and has been identified as t-butyl α-{3(S)-[1(S)-ethoxycarbonyl-3-phenylpropylamino]-2-oxo-6(R)-phenylperhydroazepin-1-yl}acetate.

$[\alpha]^{25}$ +28.1° (C=1, dimethylformamide).

Thin layer chromatography on silica gel (developing solvent cyclohexane-ethyl acetate, 3:1 by volume) Rf value=0.40.

Nuclear Magnetic Resonance Spectrum (CDCl$_3$) δ ppm: 1.25 (3H, triplet, J=7 Hz); 1.46 (9H, singlet); 1.7–2.3 (7H, multiplet); 2.5–4.1 (7H, multiplet); 4.05 (2H, AB-quartet, Δδ=0.37 ppm, J=18 Hz); 4.16 (2H, quartet, J=7 Hz); 7.0–7.4 (10H, multiplet).

1(m) t-Butyl α-{3-[1(S)-ethoxycarbonyl-3-phenylpropylamino]-2-oxo-6-phenylperhydroazepin-1-yl}acetate (Isomer B-1 and Isomer B-2 of Compound No. 5)

Using a similar procedure to that described in Example 1(l), 1.87 g of t-butyl α-[3(S*)-amino-2-oxo-6(S*)-phenylperhydroazepin-1-yl]acetate (Isomer B) [prepared as described in Example 1(k)] was N-alkylated with 2.45 g of ethyl 4-phenyl-2(R)-trifluoromethanesulfonyloxybutyrate. Isomer B-1 and Isomer B-2 were separated by silica gel column chromatography.

The isomer first eluted (Isomer B-1) was a syrup, yield 1.0 g, and has been identified as t-butyl α-{3(R)-[1(S)-ethoxycarbonyl-3-phenylpropylamino]-2-oxo-6(R)-phenylperhydroazepin-1-yl}acetate.

$[\alpha]^{25}$ −29.2° (C=1, dimethylformamide).

Thin layer chromatography on silica gel (developing solvent cyclohexane-ethyl acetate, 3:1 by volume) Rf value=0.50.

Nuclear Magnetic Resonance Spectrum (CDCl$_3$) δ ppm: 1.25 (3H, triplet, J=7 Hz); 1.44 (9H, singlet); 1.7–2.3 (7H, multiplet); 2.5–4.1 (7H, multiplet); 4.07 (2H, AB-quartet, Δδ=0.43 ppm, J=18 Hz); 4.16 (2H, quartet, J=7 Hz); 7.24 (10H, singlet).

The isomer next eluted (Isomer B-2) was a syrup, yield 1.2 g, and has been identified as t-butyl α-{3(S)-[1(S)-ethoxycarbonyl-3-phenylpropylamino]-2-oxo-6(S)-phenylperhydroazepin-1-yl}acetate.

$[\alpha]^{25}$ −11.8° (C=1, dimethylformamide).

Thin layer chromatography on silica gel (developing solvent cyclohexane-ethyl acetate, 3:1 by volume) Rf value=0.40.

Nuclear Magnetic Resonance Spectrum (CDCl$_3$) δ ppm: 1.25 (3H, triplet, J=7 Hz); 1.46 (9H, singlet); 1.7–2.3 (7H, multiplet); 2.6–4.9 (7H, multiplet); 4.07 (2H, AB-quartet, Δδ=0.34 ppm, J=18 Hz); 4.16 (2H, quartet, J=7 Hz); 7.24 (10H, singlet).

EXAMPLE 2

α-{3(S)-[1(S)-Ethoxycarbonyl-3-phenylpropylamino]-2-oxo-6(R)-phenylperhydroazepin-1-yl}acetic acid hydrochloride (Isomer A-2 of Compound No. 2))

4 ml of a 4N hydrogen chloride/dioxane solution in which was dissolved 0.95 g of t-butyl α-{3(S)-[1(S)-ethoxycarbonyl-3-phenylpropylamino]-2-oxo-6(R)-phenylperhydroazepin-1-yl}acetate (Isomer A-2) [prepared as described in Example 1(l)] were allowed to stand for 16 hours; at the end of this time, the solvent was distilled off, and the syrupy residue was mixed with a small amount of ethyl acetate and diisopropyl ether and then filtered, to give 0.80 g of the title compound as a crystalline powder, melting at 200°–202° C.

$[\alpha]^{25}$ +27.3° (C=1.1, dimethylformamide).

Nuclear Magnetic Resonance Spectrum [(CD$_3$)$_2$SO] δ ppm: 1.27 (3H, triplet, J=7 Hz); 1.7–4.9 (15H, multiplet); 4.24 (2H, quartet, J=7 Hz); 7.31 (10H, singlet).

EXAMPLE 3

α-{3(S)-[1(S)-Ethoxycarbonyl-3-phenylpropylamino]-2-oxo-6(S)-phenylperhydroazepin-1-yl}acetic acid hydrochloride (Isomer B-2 of Compound No. 2)

1.2 g of t-butyl α-{3(S)-[1(S)-ethoxycarbonyl-3-phenylpropylamino]-2-oxo-6(S)-phenylperhydroazepin-1-yl}acetate (Isomer B-2) [prepared as described in Example 1(m)] was treated in a similar manner to that described in Example 2, to afford 1.01 g of the title compound as a crystalline powder, melting at 188°–190° C.

$[\alpha]^{25}$ +48.6° (C=1.05, dimethylformamide).

Nuclear Magnetic Resonance Spectrum [(CD$_3$)$_2$SO] δ ppm: 1.29 (3H, triplet, J=7 Hz); 1.6–4.9 (15H, multiplet); 4.26 (2H, quartet, J=7 Hz); 7.29 (10H, singlet).

EXAMPLE 4

α-{3(S)-[1(S)-Carboxy-3-phenylpropylamino]-2-oxo-6(R)-phenylperhydroazepin-1-yl}acetic acid (Isomer A-2 of Compound No. 1)

3.3 ml of a 1N aqueous solution of sodium hydroxide were added to 400 mg of α-{3(S)-[1(S)-ethoxycarbonyl-3-phenylpropylamino]-2-oxo-6(R)-phenylperhydroazepin-1-yl}acetic acid hydrochloride (Isomer A-2) (prepared as described in Example 2). The reaction mixture was then stirred for 7 hours in an ice-bath, after which a 1N aqueous solution of hydrochloric acid was added to adjust its pH to a value of 2.9. The title compound which separated was collected by filtration, yielding 338 mg.

$[\alpha]^{25}$+37.1° (C=1.0, 0.1N aqueous NaOH).

Nuclear Magnetic Resonance Spectrum [(CD$_3$)$_2$SO] δ ppm: 1.6–2.2 (6H, multiplet); 2.6–4.3 (9H, multiplet); 7.28 (10H, singlet).

EXAMPLE 5

α-{3(S)-[1(S)-Carboxy-3-phenylpropylamino]-2-oxo-6(S)-phenylperhydroazepin-1-yl}acetic acid (Isomer B-2 of Compound No. 1)

400 mg of α-{3(S)-[1(S)-ethoxycarbonyl-3-phenylpropylamino]-2-oxo-6(S)-phenylperhydroazepin-1-yl}acetic acid hydrochloride (Isomer B-2) (prepared as described in Example 3) was treated in a similar manner to that described in Example 4, to afford 330 mg of the title compound as a powdery substance.

$[\alpha]^{25}+51.7°$ (C=1, 0.1N aqueous NaOH).

Nuclear Magnetic Resonance Spectrum [(CD$_3$)$_2$SO] δ ppm: 1.6–2.2 (6H, multiplet); 2.6–4.8 (9H, multiplet); 7.1–7.4 (10H, multiplet).

EXAMPLE 6 t-Butyl α-{3-[1(S)-ethoxycarbonyl-3-phenylpropylamino]-6-(p-fluorophenyl)-2-oxoperhydroazepin-1-yl}acetate (isomer of Compound No. 96)

6(a) 6-(p-Fluorophenyl)perhydroazepin-2-one

The procedure described in Example 1(a)–(d) was repeated, but using p-fluorophenylacetonitrile in place of phenylacetonitrile to give the title compound as crystals, melting at 158°–160° C.

Nuclear Magnetic Resonance Spectrum (CDCl$_3$) δ ppm: 1.5–2.3 (4H, multiplet); 2.4–2.7 (2H, multiplet); 2.7–3.7 (3H, multiplet); 6.8–7.3 (5H, multiplet).

6(b) 3-Bromo-6-(p-fluorophenyl)perhydroazepin-2-one

Using the same procedure as described in Example 1(e), the title compound was prepared as crystals melting at 218° C. (with coloration over 210° C.) from 6-(p-fluorophenyl)perhydroazepin-2-one [prepared as described in step (a) above].

Nuclear Magnetic Resonance Spectrum [(CD$_3$)$_2$SO] δ ppm: 1.7–2.3 (4H, multiplet); 2.5–3.85 (3H, multiplet); 4.71 (1H, multiplet); 7.0–7.4 (4H, multiplet); 7.97 (1H, multiplet).

6(c) 3(S*)-Azido-6(R*)-(p-fluorophenyl)perhydroazepin-2-one

Using a similar procedure to that described in Example 1(f), the title compound was prepared as crystals melting at 103°–104.5° C. from 3-bromo-6-(p-fluorophenyl)perhydroazepin-2-one [prepared as described in step (b) above].

Nuclear Magnetic Resonance Spectrum (CDCl$_3$) δ ppm: 1.6–2.3 (4H, multiplet); 2.4–2.9 (1H, multiplet); 3.0–3.7 (2H, multiplet); 4.13 (1H, multiplet); 6.8–7.5 (5H, multiplet).

6(d) t-Butyl α-[3(S*)-azido-6(R*)-(p-fluorophenyl)-2-oxoperhydroazepin-1-yl]acetate According to a similar procedure to that described in Example 1(h), 3(S*)-azido-6(R*)-(p-fluorophenyl)perhydroazepin-2-one [prepared as described in step (c) above] gave the title compound as crystals, melting at 135.5°–137° C.

Nuclear Magnetic Resonance Spectrum (CDCl$_3$) δ ppm: 1.47 (9H, singlet); 1.75–2.3 (4H, multiplet); 2.8–4.3 (4H); 4.11 (2H, AB-quartet, Δδ=0.33 ppm, J=17 Hz); 6.85–7.3 (4H, multiplet).

6(e) t-Butyl α-[3(S*)-amino-6(R*)-(p-fluorophenyl)-2-oxoperhydroazepin-1-yl]acetate According to a similar procedure to that described in Example 1(j), the title compound was prepared as a gum from t-butyl α-[3(S*)-azido-6(R*)-(p-fluorophenyl)-2-oxoperhydrothiazepin-1-yl]acetate [prepared as described in step (d) above].

Nuclear Magnetic Resonance Spectrum (CDCl$_3$) δ ppm: 1.48 (9H, singlet); 1.62 (2H, broad singlet); 1.5–2.3 (4H, multiplet); 2.7–4.1 (4H, multiplet); 4.11 (2H, AB-quartet, Δδ=0.32 ppm, J=17 Hz); 6.8–7.3 (4H, multiplet).

6(f) t-Butyl α-}3-[1(S)-ethoxycarbonyl-3-phenylpropylamino]-6-(p-fluorophenyl)-2-oxoperhydroazepin-1-yl}acetate According to a similar procedure to that described in Example 1(l), t-butyl α-[3(S*)-amino-6(R*)-(p-fluorophenyl)-2-oxoperhydroazepin-1-yl]acetate [prepared as described in step (e) above] was reacted with ethyl 4-phenyl-2(R)-trifluoromethanesulfonyloxyacetate, to give a crude product, which was subjected to column chromatography through silica gel using a 4:1 by volume mixture of cyclohexane and ethyl acetate as eluent.

t-Butyl α{3(R)-[1(S)-ethoxycarbonyl-3-phenylpropylamino]-6(S)-(p-fluorophenyl)-2-oxoperhydroazepin-1-yl}acetate was eluted first.

Nuclear Magnetic Resonance Spectrum (CDCl$_3$) δ ppm: 1.26 (3H, triplet, J=7 Hz); 1.47 (9H, singlet); 1.7–2.25 (7H, multiplet); 2.6–3.9 (7H, multiplet); 4.09 (2H, AB-quartet, Δδ=0.43 ppm, J=17 Hz); 4.18 (2H, quartet, J=7 Hz); 6.9–7.3 (4H, multiplet); 7.23 (5H, singlet).

Subsequently, t-butyl α-{3(S)-[1(S)-ethoxycarbonyl-3-phenylpropylamino]-6(R)-(p-fluorophenyl)-2-oxoperhydroazepin-1-yl}acetate was eluted.

Nuclear Magnetic Resonance Spectrum (CDCl$_3$) δ ppm; 1.28 (3H, triplet, J=7 Hz); 1.47 (9H, singlet); 1.7–2.3 (7H, multiplet); 2.5–4.0 (7H, multiplet); 4.09 (2H, AB-quartet, Δδ=0.41 ppm, J=17 Hz); 4.18 (2H, quartet, J=7 Hz); 6.85–7.3 (4H, multiplet); 7.23 (5H, singlet).

EXAMPLE 7

α-{3(S)-[1(S)-Ethoxycarbonyl-3-phenylpropylamino]-6(R)-(p-fluorophenyl)-2-oxoperhydroazepin-1-yl}acetic acid hydrochloride (isomer of Compound No. 85, hydrochloride)

According to a similar procedure to that described in Example 2, the title compound, melting at 181°–183° C., was prepared from t-butyl α-{3(S)-[1(S)-ethoxycarbonyl-3-phenylpropylamino]-6(R)-(p-fluorophenyl)-2-oxoperhydroazepin-1-yl}acetate [the second compound to be eluted in Example 6(f)].

$[\alpha]^{25}+25.5°$ (C=1, dimethylformamide).

Nuclear Magnetic Resonance Spectrum [(CD$_3$)$_2$SO] δ ppm: 1.28 (3H, triplet, J=7 Hz); 1.74–4.75 (15H, multiplet); 4.26 (2H, quartet, J=7 Hz); 7.0–7.5 (4H, multiplet); 7.31 (5H, singlet).

EXAMPLE 8

α-{3(S)-[1(S)-Carboxy-3-phenylpropylamino]-6(R)-(p-fluorophenyl)-2-oxoperhydroazepin-1-yl}acetic acid (isomer of Compound No. 84)

According to a similar procedure to that described in Example 4, the title compound was synthesized as a powder from α-{3(S)-[1(S)-ethoxycarbonyl-3-phenylpropylamino]-6(R)-(p-fluorophenyl)-2-oxoperhydroazepin-1-yl}acetic acid hydrochloride (prepared as described in Example 7).

$[\alpha]^{25}+31.4°$ (C=1, 0.1N aqueous NaOH).

Nuclear Magnetic Resonance Spectrum [(CD$_3$)$_2$SO] δ ppm: 1.6–2.2 (6H, multiplet); 2.5–4.6 (9H, multiplet); 7.0–7.45 (4H, multiplet); 7.28 (5H, singlet).

EXAMPLE 9 t-Butyl
α-{3[1(S)-butoxycarbonyl-3-phenylpropylamino]-6-(p-fluorophenyl)-2-oxoperhydroazepin-1-yl}acetate
(isomer of Compound No. 97)

According to a similar procedure to that described in Example 1(I), t-butyl α-[3(S*)-amino-6(R*)-(p-fluorophenyl)-2-oxoperhydroazepin-1-yl]acetate [prepared as described in Example 6(e)] was reacted with butyl 4-phenyl-2(R)-trifluoromethanesulfonyloxybutyrate, to give a crude product, which was subjected to column chromatography through silica gel using a 3:1 by volume mixture of cyclohexane and ethyl acetate as eluent.

First, t-butyl α-{3(R)-[1(S)-butoxycarbonyl-3-phenylpropylamino]-6(S)-(p-fluorophenyl)-2-oxo-perhydroazepin-1-yl}acetate was eluted.

Nuclear Magnetic Resonance Spectrum (CDCl$_3$) δ ppm: 0.7–1.1 (3H, multiplet); 1.46 (9H, singlet); 1.2–2.2 (10H, multiplet); 2.5–4.2 (9H, multiplet); 4.16 (2H, AB-quartet, Δδ=0.33 ppm, J=17 Hz); 6.9–7.3 (4H, multiplet); 7.22 (5H, singlet).

Subsequently, t-butyl α-{3(S)-[1(S)-butoxycarbonyl-3-phenylpropylamino]-6(R)-(p-fluorophenyl)-2-oxoperhydroazepin-1-yl}acetate was eluted.

Nuclear Magnetic Resonance Spectrum (CDCl$_3$) δ ppm: 0.7–1.1 (3H, multiplet); 1.48 (9H, singlet); 1.2–2.3 (10H, multiplet); 2.5–4.3 (9H, multiplet); 4.09 (2H, AB-quartet, Δδ=0.41 ppm, J=17 Hz); 6.9–7.3 (4H, multiplet); 7.22 (5H, singlet).

EXAMPLE 10

α-{3(S)-[1(S)-Butoxycarbonyl-3-phenylpropylamino]-6(R)-(p-fluorophenyl)-2-oxoperhydroazepin-1-yl}acetic acid hydrochloride (isomer of Compound No. 86, hydrochloride)

According to a similar procedure to that described in Example 2, the title compound, melting at 207° C., was prepared from t-butyl α-{3(S)-[1(S)-butoxycarbonyl-3-phenylpropylamino]-6(R)-(p-fluorophenyl)-2-oxoperhydroazepin-1-yl}acetate [the second compound to be eluted in Example 9].

$[\alpha]^{25} - 23.4°$ (C=1, dimethylformamide).

Nuclear Magnetic Resonance Spectrum [(CD$_3$)$_2$SO] δ ppm: 0.93 (3H, broad triplet, J=6.5 Hz); 1.15–2.4 (10H, multiplet); 2.6–4.75 (11H, multiplet); 7.0–7.5 (4H, multiplet); 7.32 (5H, singlet).

EXAMPLE 11 t-Butyl
α-{3-[1(S)-butoxycarbonyl-3-phenylpropylamino]-2-oxo-6-phenylperhydroazepin-1-yl}acetate (isomer of Compound No. 98)

According to a similar procedure to that described in Example 1(I), 1.62 g of t-butyl α-[3(S*)-amino-2-oxo-6(S*)-phenylperhydroazepin-1-yl]acetate [prepared as described in Example 1(j)] was N-alkylated with 2.24 g of butyl 4-phenyl-2-(R)-trifluoromethanesulfonyloxybutyrate, and the resulting product was subjected to silica gel column chromatography, using a 3:1 by volume mixture of cyclohexane and ethyl acetate as eluent.

First, 1.15 g of t-butyl α-{3(R)-[1(S)-butoxycarbonyl-3-phenylpropylamino]-2-oxo-6(S)-phenylperhydroazepin-1-yl}acetate was obtained as an oil.

$[\alpha]^{25} - 42.8°$ (C=1, dimethylformamide).

Nuclear Magnetic Resonance Spectrum (CDCl$_3$) δ ppm: 0.7–1.1 (3H, multiplet); 1.48 (9H, singlet); 1.2–2.25 (10H, multiplet); 2.6–4.25 (9H, multiplet); 4.06 (2H, AB-quartet, Δδ=0.42 ppm, J=17 Hz); 7.26 (10H, singlet).

Then, 1.25 g of t-butyl α-}3(S)-[1(S)-butoxycarbonyl-3-phenylpropylamino]-2-oxo-6(R)-phenylperhydroazepin-1-yl}acetate was obtained as an oil.

$[\alpha]^{25} + 28.2°$ (C=1, dimethylformamide).

Nuclear Magnetic Resonance Spectrum (CDCl$_3$) δ ppm: 0.7–1.1 (3H, multiplet); 1.47 (9H, singlet); 1.2–2.25 (10H, multiplet); 2.36 (1H, broad singlet); 2.5–4.25 (9H, multiplet); 4.08 (2H, AB-quartet, Δδ=0.34 ppm, J=17 Hz); 7.24 (10H, singlet).

EXAMPLE 12

α-{3(S)-[1(S)-Butoxycarbonyl-3-phenylpropylamino]-2-oxo-6(R)-phenylperhydroazepin-1-yl}acetic acid hydrochloride (isomer of Compound No. 3, hydrochloride)

Following the same procedure as described in Example 2, 1.1 g of t-butyl α-{3-[3(S)-[1(S)-butoxycarbonyl-3-phenylpropylamino]-2-oxo-6(R)-phenylperhydroazepin-1-yl}acetate (the second compound to be eluted in Example 11) gave 0.85 g of the title compound as a crystalline powder, melting at 167°–168.5° C.

$[\alpha]^{25} + 25.3°$ (C=1, dimethylformamide).

Nuclear Magnetic Resonance Spectrum [(CD$_3$)$_2$SO] δ ppm: 0.93 (3H, broad triplet, J=6.5 Hz); 1.2–2.5 (10H, multiplet); 2.5–4.75 (11H, multiplet); 7.33 (10H, singlet).

We claim:

1. A compound of formula (I):

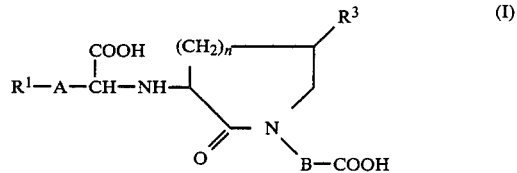

in which:

R$^1$ represents a C$_1$–C$_{10}$ alkyl group, a C$_3$–C$_8$ cycloalkyl group, an aryl group or a heterocyclic group, or said alkyl group having at least one substituent selected from the group consisting of substituents (a) or said cycloalkyl, aryl or heterocyclic group having at least one substituent selected from the group consisting of substituents (a) and substituents (b);

R$^3$ represents a C$_1$–C$_{10}$ alkyl group, a C$_3$–C$_8$ cycloalkyl group, an aralkyl group wherein the alkyl part is C$_1$–C$_6$ alkyl, an aryl group, a C$_1$–C$_6$ alkyl group having a heterocyclic substituent or a heterocyclic group, where said heterocyclic group or said heterocyclic substituent is selected from the group consisting of tetrahydrofuranyl, tetrahydrothienyl, tetrahydropyranyl, morpholinyl, furyl, thienyl, imidazolyl, thiazolyl, oxazolyl, isoxazolyl, oxadiazolyl, thiadiazolyl, pyridyl, quinolyl, isoquinolyl and indolyl, or said alkyl group having at least one substituent selected from the group consisting of substituents (a) or said cycloalkyl, aryl or heterocyclic group having at least one substituent selected from the group consisting of substituents (a) and (b);

A represents a single bond, a methylene group, an ethylene group or a group of formula —CO—CH$_2$—, —O—CH$_2$— or —S—CH$_2$—;

B represents an alkylene group having from 1 to 4 carbon atoms;

n is an integer from 1 to 3;

substituents (a) are:

hydroxy groups, $C_1$-$C_6$ alkoxy groups, an aryl group having from 0 to 3 substituents selected from the group consisting of substituents (a) and substituents (b), aralkyloxy groups where the alkyl part is $C_1$-$C_6$ alkyl and the aryl part has from 0 to 3 substituents selected from the group consisting of substituents (a) and (b), aryloxy groups, halogen atoms, nitro groups, cyano groups, carboxy groups, alkoxycarbonyl groups having a total of from 2 to 7 carbon atoms, amino groups, $C_1$-$C_6$ alkylamino groups, dialkylamino groups wherein each alkyl part is $C_1$-$C_6$ alkyl, $C_1$-$C_6$ aliphatic or carbocyclic aryl acylamino groups carbamoyl groups, alkylcarbamoyl groups where the alkyl part is $C_1$-$C_6$ alkyl, dialkylcarbamoyl groups where each alkyl part is $C_1$-$C_6$ alkyl, mercapto groups, $C_1$-$C_6$ alkylthio groups, arylthio groups, $C_1$-$C_6$ alkylsulfonyl groups and arylsulfonyl groups wherein the aryl part has from 0 to 3 $C_1$-$C_6$ alkyl substituents;

substituents (b) are:

$C_1$-$C_6$ alkyl groups and aralkyl groups wherein the alkyl part is $C_1$-$C_6$ alkyl and the aryl part has from 0 to 3 substituents selected from the group consisting of substituents (a) and substituents (b); and said aryl and said aryl part of said aralkyl, aralkyloxy, aryloxy, aryl acylamino, arylthio or arylsulfonyl is phenyl or naphthyl;

and pharmaceutically acceptable salts and esters thereof.

2. The compound as claimed in claim 1, having the formula (Ia):

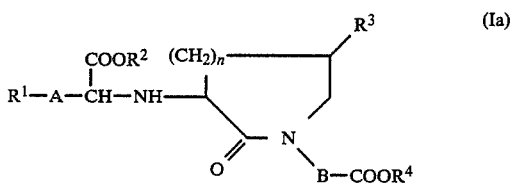

wherein $R^1$, $R^3$, A, B and n are as defined in claim 1 and $R^2$ and $R^4$ are independently selected from the group consisting of hydrogen $C_1$-$C_6$ alkyl, benzyl, benzhydryl, 1-indanyl, 2-indanyl, 1- or 2-(1,2,3,4-tetrahydronaphthyl), phthalidyl, phenyl, naphthyl, tri($C_1$-$C_4$ alkyl)silyl, 2,2,2-trichloroethyl, 2-iodoethyl, 2-hydroxyethyl, 2,3-dihydroxypropyl, methoxymethyl, 2-methoxyethoxymethyl, p-methoxybenzyl, acetoxymethyl, 1-acetoxyethyl, pivaloyloxymethyl, phenacyl, methoxycarbonylmethyl, ethoxycarbonylethyl, ethoxycarbonyloxymethyl, 1-(ethoxycarbonyloxy)ethyl, p-nitrobenzyl, 1-cyanoethyl, 2-cyanoethyl, methylthiomethyl, ethylthiomethyl, phenylthiomethyl, 2-methanesulfonylethyl, 2-benzenesulfonylethyl, (5-methyl-2-oxo-1,3-dioxolen-4-yl)methyl, and (5-phenyl-2-oxo-1,3-dioxolen-4-yl)methyl.

3. The compound as claimed in claim 2, wherein $R^2$ and $R^4$ are independently selected from the group consisting of $C_1$-$C_{10}$ alkyl groups, aralkyl groups in which the aryl part is unsubstituted or substituted as defined in (c) below and the alkyl part is $C_1$-$C_6$ alkyl, aryl groups, phthalidyl groups and substituted silyl groups, said groups represented by $R^2$ and $R^4$ being unsubstituted or having at least one substituent selected from the group consisting of:

(c) $C_1$-$C_6$ alkyl groups except where the parent group is an alkyl group, halogen atoms, hydroxy groups, $C_1$-$C_6$ alkoxy groups, $C_1$-$C_3$ alkoxy groups substituted by a $C_1$-$C_6$ alkoxy group, $C_1$-$C_6$ aliphatic and aryl acyloxy groups, oxo groups, carboxy groups, alkoxycarbonyl groups where the alkoxy part is $C_1$-$C_6$ alkoxy, alkoxycarbonyloxy groups where the alkoxy part is $C_1$-$C_6$ alkoxy, $C_1$-$C_6$ aliphatic and aryl acylamino groups, nitro groups, cyano groups, amino groups, $C_1$-$C_6$ alkylamino groups, dialkylamino groups where each alkyl part is $C_1$-$C_6$ alkyl, arylamino groups, mercapto groups, $C_1$-$C_6$ alkylthio groups, arylthio groups, $C_1$-$C_6$ alkylsulfonyl groups, arylsulfonyl groups and heterocyclic groups selected from the group consisting of tetrahydrofuranyl, tetrahydrothienyl, tetrahydropyranyl, morpholinyl, furyl, thienyl, imidazolyl, thiazolyl, oxazolyl, isoxazolyl, oxadiazolyl, thiadiazolyl, pyridyl, quinolyl, isoquinolyl and indolyl, said heterocyclic groups being unsubstituted or having at least one substituent selected from the group consisting of the substituents (a) and (b).

4. The compound as claimed in claim 2, wherein $R^2$ represents a hydrogen atom; a straight or branched chain alkyl group having from 1 to 6 carbon atoms; an aralkyl group wherein the alkyl part is $C_1$-$C_6$ alkyl and the aryl part is phenyl or naphthyl or a protecting group selected from the group consisting of acetoxymethyl, pivaloyloxymethyl, phthalidyl, 1-(ethoxycarbonyloxy)ethyl, and (5-methyl-2-oxo-1,3-dioxolen-4-yl)methyl.

5. The compound as claimed in claim 2, wherein $R^2$ represents a hydrogen atom or a methyl, ethyl, propyl, isopropyl, butyl, isobutyl, pentyl, hexyl, benzyl, acetoxymethyl, pivaloyloxymethyl, phthalidyl, 1-(ethoxycarbonyloxy)ethyl or (5-methyl-2-oxo-1,3-dioxolen-4-yl)methyl group.

6. The compound as claimed in claim 2, wherein $R^4$ represents a t-butyl, methoxymethyl, 2,2,2-trichloroethyl, benzyl, p-methoxybenzyl, diphenylmethyl, acetoxymethyl, pivaloyloxymethyl, 1-(ethoxycarbonyloxy)ethyl, phthalidyl or (5-methyl-2-oxo-1,3-dioxolen-4-yl)methyl group.

7. The compound as claimed in claim 3, wherein:

$R^1$—A— represents a straight or branched chain alkyl group having from 4 to 9 carbon atoms; a cycloalkylethyl group in which the cycloalkyl part has 5 or 6 ring carbon atoms; an aralkyl group wherein the alkyl part is $C_1$-$C_2$ alkyl and the aryl part is phenyl or naphthyl; a phenoxymethyl group, a phenylthiomethyl group; a 2-(2-thienyl)ethyl group; a 2-(2-imidazolyl)ethyl group; or a 2-(2-thiazolyl)ethyl group;

$R^3$ represents a straight or branched chain alkyl group having from 1 to 6 carbon atoms; a cycloalkyl group having 5 or 6 ring carbon atoms; an aralkyl group wherein the alkyl part is $C_1$-$C_2$ alkyl and the aryl part is phenyl or naphthyl; an aryl group; a heterocyclylmethyl group; or a heterocyclic group;

B represents a methylene group; and n is 2 or 3.

8. The compound as claimed in claim 2, wherein:

$R^1$ represents a $C_4$-$C_7$ alkyl group, a $C_5$-$C_6$ cycloalkyl group, a phenyl group or a phenyl group having at least one substituent selected from the group consisting of substituents (a) and (b);

$R^2$ represents a hydrogen atom, a $C_1$-$C_4$ alkyl group or a benzyl group;

$R^3$ represents a $C_3$–$C_6$ alkyl group, a phenyl group or a phenyl group having at least one substituent selected from the group consisting of substituents (a) and (b);

$R^4$ represents a hydrogen atom, a $C_1$–$C_4$ alkyl group, a benzyl group, a p-methoxybenzyl group or a diphenylmethyl group;

A represents a $C_1$ or $C_2$ alkylene group;

B represents a methylene group; and n is 2.

9. The compound as claimed in claim 2, wherein:

$R^1$ represents a butyl group, a pentyl group, a hexyl group, a cyclohexyl group or a phenyl group;

$R^2$ represents a hydrogen atom, a $C_2$–$C_4$ alkyl group or a benzyl group;

$R^3$ represents a phenyl group or a halophenyl group;

$R^4$ represents a hydrogen atom, a $C_2$–$C_4$ alkyl group; a p-methoxybenzyl group or a diphenylmethyl group;

A represents an ethylene group;

B represents a methylene group; and n is 2.

10. t-butyl α-[3-(1-ethoxycarbonyl-3-phenylpropylamino)-2-oxo-6-phenylperhydroazepin-1-yl]acetate.

11. α-[3-(1-ethoxycarbonyl-3-phenylpropylamino)-2-oxo-6-phenylperhydroazepin-1-yl]acetic acid.

12. α-[3-(1-carboxy-3-phenylpropylamino)-2-oxo-6-phenylperhydroazepin-1-yl]acetic acid.

13. t-butyl α-[3-(1-ethoxycarbonyl-3-phenylpropylamino)-6-(p-fluorophenyl)-2-oxoperhydroazepin-1-yl]acetate.

14. α-[3-(1-ethoxycarbonyl-3-phenylpropylamino)-6-(p-fluorophenyl)-2-oxoperhydroazepin-1-yl]acetic acid.

15. α-[3-(1-carboxy-3-phenylpropylamino)-6-(p-fluorophenyl)-2-oxoperhydroazepin-1-yl]acetic acid.

16. t-butyl α-[3-(1-butoxycarbonyl-3-phenylpropylamino)-6-(p-fluorophenyl)-2-oxoperhydroazepin-1-yl]acetate.

17. α-[3-(1-butoxycarbonyl-3-phenylpropylamino)-6-(p-fluorophenyl)-2-oxoperhydroazepin-1-yl]acetic acid.

18. t-butyl α-[3-(1-butoxycarbonyl-3-phenylpropylamino)-2-oxo-6-phenylperhydroazepin-1-yl]acetate.

19. α-[3-(1-butoxycarbonyl-3-phenylpropylamino)-2-oxo-6-phenylperhydroazepin-1-yl]acetic acid.

20. α-{3(S)-[1(S)-ethoxycarbonyl-3-phenylpropylamino]-2-oxo-6(R)-phenylperhydroazepin-1-yl}acetic acid.

21. α-{3(S)-[1(S)-carboxy-3-phenylpropylamino]-2-oxo-6(R)-phenylperhydroazepin-1-yl}acetic acid.

22. α-{3(S)-[1(S)-ethoxycarbonyl-3-phenylpropylamino]-6(R)-(p-fluorophenyl)-2-oxoperhydroazepin-1-yl}acetic acid.

23. α-{3(S)-[1(S)-carboxy-3-phenylpropylamino]-6(R)-(p-fluorophenyl)-2-oxoperhydroazepin-1-yl}acetic acid.

24. α-{3(S)-[1(S)-butoxycarbonyl-3-phenylpropylamino]-6(R)-(p-fluorophenyl)-2-oxoperhydroazepin-1-yl}acetic acid.

25. α-{3(S)-[1(S)-butoxycarbonyl-3-phenylpropylamino]-2-oxo-6(R)-phenylperhydroazepin-1-yl}acetic acid.

26. A pharmaceutical composition for the treatment of angiotensin-induced hypertension, which composition comprises an effective amount of a hypotensive agent in admixture with a pharmaceutically acceptable carrier or diluent, wherein said hypotensive agent is selected from the group consisting of compounds of formula (I) and pharmaceutically acceptable salts and esters thereof as claimed in claim 1.

27. A method of treating angiotensin-induced hypertension in a mammal by administering to said mammal an effective amount of a hypotensive agent, wherein said hypotensive agent is selected from the group consisting of compounds of formula (I) and pharmaceutically acceptable salts and esters thereof as claimed in claim 1.

* * * * *

UNITED STATES PATENT AND TRADEMARK OFFICE
CERTIFICATE OF CORRECTION

PATENT NO. : 4,734,410
DATED : March 29, 1988
INVENTOR(S) : YANAGISAWA ET AL

It is certified that error appears in the above-identified patent and that said Letters Patent is hereby corrected as shown below:

Title page:

Under "U.S. PATENT DOCUMENTS":

Change "4,699,905 11/1987" to --4,699,905 10/1987--.

Under "FOREIGN PATENT DOCUMENTS":

Change "0161801...428/312.6" to --0161801...540/488--.

Signed and Sealed this

Twenty-sixth Day of May, 1992

Attest:

DOUGLAS B. COMER

*Attesting Officer*  *Acting Commissioner of Patents and Trademarks*